United States Patent
Chockalingam et al.

(10) Patent No.: US 12,163,956 B2
(45) Date of Patent: Dec. 10, 2024

(54) LATERAL FLOW IMMUNOASSAY FOR MEASURING FUNCTIONAL C1-ESTERASE INHIBITOR (C1-INH) IN PLASMA SAMPLES

(71) Applicant: Takeda Pharmaceutical Company Limited, Osaka (JP)

(72) Inventors: Priya Sethu Chockalingam, Sudbury, MA (US); Zhiwei Zhou, Boston, MA (US)

(73) Assignee: Takeda Pharmaceutical Company Limited, Osaka (JP)

(*) Notice: Subject to any disclaimer, the term of this patent is extended or adjusted under 35 U.S.C. 154(b) by 963 days.

(21) Appl. No.: 16/844,463

(22) Filed: Apr. 9, 2020

(65) Prior Publication Data
US 2020/0340987 A1 Oct. 29, 2020

Related U.S. Application Data

(60) Provisional application No. 62/833,235, filed on Apr. 12, 2019.

(51) Int. Cl.
*G01N 33/543* (2006.01)
*G01N 21/64* (2006.01)
*G01N 33/58* (2006.01)

(52) U.S. Cl.
CPC ... *G01N 33/54388* (2021.08); *G01N 21/6428* (2013.01); *G01N 33/54366* (2013.01);
(Continued)

(58) Field of Classification Search
CPC ......... G01N 33/54388; G01N 21/6428; G01N 33/54366; G01N 33/582; G01N 33/588;
(Continued)

(56) References Cited

U.S. PATENT DOCUMENTS

| 4,855,240 A | 8/1989 | Rosenstein et al. |
| 7,001,775 B1 * | 2/2006 | Burne ............... G01N 33/54388 436/805 |

(Continued)

FOREIGN PATENT DOCUMENTS

| CN | 101137412 A | 3/2008 |
| CN | 102307594 A | 1/2012 |

(Continued)

OTHER PUBLICATIONS

Ineke G.A. Wagenaar-Bos et al., Functional C1-Inhibitor diagnostics in hereditary angioedema: Assay evaluation and recommendations, Sep. 30, 2008, pp. 14-20 (Year: 2008).*

(Continued)

*Primary Examiner* — Christopher L Chin
(74) *Attorney, Agent, or Firm* — Wolf, Greenfield & Sacks, P.C.

(57) ABSTRACT

A device for detecting and/or quantifying functional C1-esterase inhibitor (fC1-INH), the device comprising: (i) a conjugate pad comprising a first zone and a second zone, on which a first agent and a second agent are immobilized, respectively, and (ii) a membrane, which is in communication with the conjugate pad, wherein the membrane comprises a third zone, on which a third agent is immobilized. The conjugate pad may further comprise a fourth zone for placing a biological sample, which flows through the device in the order of the first zone, the second zone, and the third zone.

20 Claims, 14 Drawing Sheets

(52) U.S. Cl.
CPC ......... *G01N 33/582* (2013.01); *G01N 33/588* (2013.01); *G01N 2021/6439* (2013.01); *G01N 2458/00* (2013.01); *G01N 2800/24* (2013.01)

(58) Field of Classification Search
CPC ....... G01N 2021/6439; G01N 2458/00; G01N 2800/24; G01N 2333/8121; G01N 33/558; G01N 33/54387; G01N 33/54389; G01N 2333/81; B01L 2300/0825
USPC ....... 422/400, 401, 420, 421, 425, 426, 430; 435/287.7, 287.9, 970, 805, 810; 436/169, 170, 514, 518, 530, 810
See application file for complete search history.

(56) References Cited

U.S. PATENT DOCUMENTS

| | | |
|---|---|---|
| 11,754,570 B2 | 9/2023 | Chockalingam et al. |
| 11,892,450 B2 | 2/2024 | Joseph et al. |
| 2009/0064350 A1 | 3/2009 | Dewald |
| 2010/0119512 A1 | 5/2010 | Feener et al. |
| 2012/0201756 A1 | 8/2012 | Sexton |
| 2014/0335023 A1 | 11/2014 | Sexton et al. |
| 2020/0348311 A1 | 11/2020 | Chockalingam et al. |
| 2020/0355700 A1 | 11/2020 | Cozma |
| 2020/0393464 A1 | 12/2020 | Joseph et al. |

FOREIGN PATENT DOCUMENTS

| | | |
|---|---|---|
| EP | 1598428 A1 | 11/2005 |
| JP | 2002-528722 A | 9/2002 |
| JP | 2016-511394 A | 4/2016 |
| JP | 2019-501886 A | 1/2019 |
| RU | 2139099 C1 | 10/1999 |
| WO | 2006/091459 A2 | 8/2006 |
| WO | 2008/073222 A2 | 6/2008 |
| WO | 2008/098720 A1 | 8/2008 |
| WO | 2014/113701 A1 | 7/2014 |
| WO | 2014/159637 A1 | 10/2014 |
| WO | 2015/112578 A1 | 7/2015 |
| WO | 2019/149816 A1 | 8/2019 |
| WO | 2020/210446 A1 | 10/2020 |

OTHER PUBLICATIONS

Vajdos et al., "Comprehensive functional maps of the antigen-binding site of an anti-ErbB2 antibody obtained with shotgun scanning mutagenesis" J Mol Biol. Jul. 5, 2002;320(2):415-28, DOI: 10.1016/S0022-2836(02)00264-4 (Year: 2002).*
Almagro et al., "Humanization of Antibodies", Frontiers in Bioscience 13, 1619-1633 (Year: 2008).*
Goel Manisha et al., "Plasticity within the Antigen-Combining Site May Manifest as Molecular Mimicry in the Humoral Immune Response", The Journal of Immunology 173(12):7358-7367 (Year: 2004).*
Edwards et al., "The remarkable flexibility of the human antibody repertoire; isolation of over one thousand different antibodies to a single protein, BLyS" J. Mol. Biol. (2003) 334, 103-118, DOI: 10.1016/j.jmb.2003.09.054 (Year: 2003).*
Edwards, Lloyd et al. "Modelling the human immune response: performance of a 10e11 human antibody repertoire against a broad panel of therapeutically relevant antigens", Protein Engineering, Design and Selection, vol. 22, Issue 3, Mar. 1, 2009, pp. 159-168, https://doi.org/10.1093/protein/gzn058 (Year: 2009).*
Brown et al., "Tolerance of single, but not multiple, amino acid replacements in antibody VH CDR 2: a means of minimizing B cell wastage from somatic hypermutation?", J Immunol. May 1996;156(9):3285-91 (Year: 1996).*
Alsenz et al., Simplified methods for the purification, quantitation, and functional estimation of human complement C-1-inhibitor (C-1-INH) with a monoclonal anti-C-1-INH antibody. J Immunol Methods. Jan. 26, 1987;96(1):107-14. doi: 10.1016/0022-1759(87)90373-5.
Biomarkers Definitions Working Group. Biomarkers and surrogate endpoints: preferred definitions and conceptual framework. Clin Pharmacol Ther. Mar. 2001;69(3):89-95. doi: 10.1067/mcp.2001.113989.
Caballero et al., Consensus statement on the diagnosis, management, and treatment of angioedema mediated by bradykinin. Part II. Treatment, follow-up, and special situations. J Investig Allergol Clin Immunol. 2011;21(6):422-41.
Chen et al., Enhancement and destruction of antibody function by somatic mutation: unequal occurrence is controlled by V gene combinatorial associations. Embo J. Jun. 1, 19955;14(12):2784-94. doi: 10.1002/j.1460-2075.1995.tb07278.x.
Chockalingam et al., A first of its kind quantitative functional C1-esterase inhibitor lateral flow assay for hereditary angioedema point-of-care diagnostic testing. Int Immunopharmacol. Jun. 1, 2020;83:106526(1-6). doi: 10.1016/j.intimp.2020.106526. Epub Apr. 3, 20200.
Colman P.M., Effects of amino acid sequence changes on antibody-antigen interactions. Res Immunol. Jan. 1994;145(1):33-6. doi: 10.1016/s0923-2494(94)80039-1.
D'ANGELO et al., Many Routes to an Antibody Heavy-Chain CDR3: Necessary, Yet Insufficient, for Specific Binding. Front Immunol. Mar. 8, 2018;9:395. doi: 10.3389/fimmu.2018.00395. Supplementary Information, 46 pages.
Feussner et al., Biochemical comparison of four commercially available C1 esterase inhibitor concentrates for treatment of hereditary angioedema. Transfusion. Oct. 2014;54(10):2566-73. doi: 10.1111/trf.12678. Epub May 8, 2014.
Kasthuri et al., Potential biomarkers of an exaggerated response to endotoxemia. Biomarkers. May 2007-Jun. 12(3):287-302. doi: 10.1080/13547500601160536.
Kussie et al., A single engineered amino acid substitution changes antibody fine specificity. J Immunol. Jan. 1, 1994;152(1):146-52.
Lai et al., A novel functional C1 inhibitor activity assay in dried blood spot for diagnosis of Hereditary angioedema. Clin Chim Acta. May 2020;504:155-162. doi: 10.1016/j.cca.2020.02.010. Epub Feb. 1, 20202.
Li et al., Comparison of chromogenic and ELISA functional C1 inhibitor tests in diagnosing hereditary angioedema. J Allergy Clin Immunol Pract. Mar. 2015-Apr;3(2):200-5. doi: 10.1016/j.jaip.2014.08.002. Epub Oct. 1, 20141.
Mandle et al., Acquired C1 inhibitor deficiency as a result of an autoantibody to the reactive center region of C1 inhibitor. J Immunol. May 1, 1994;152(9):4680-5.
Martin et al., Dried blood spot proteomics: surface extraction of endogenous proteins coupled with automated sample preparation and mass spectrometry analysis. J Am Soc Mass Spectrom. Aug. 2013;24(8):1242-9. doi: 10.1007/s13361-013-0658-1. Epub Jun. 1, 2013.
Nuijens et al., Quantification of plasma factor XIIa-Cl(-)-inhibitor and kallikrein-CI(-)- inhibitor complexes in sepsis. Blood. Dec. 1988;72(6): 1841-8.
Prince H.E., Biomarkers for diagnosing and monitoring autoimmune diseases. Biomarkers. Nov. 2005; 10 Suppl 1:S44-9. doi: 10.1080/13547500500214194.
Rudikoff et al., Single amino acid substitution altering antigen-binding specificity. Proc Natl Acad Sci U S A. Mar. 1982;79(6): 1979-83. doi: 10.1073/pnas.79.6.1979.
Varga et al., rhC1INH: a new drug for the treatment of attacks in hereditary angioedema caused by C1-inhibitor deficiency. Expert Rev Clin Immunol. 2011;7(2):143-153. Epub Jan. 10, 2014.
Wagenaar-Bos et al., Functional C1-inhibitor diagnostics in hereditary angioedema: assay evaluation and recommendations. J Immunol Methods. Sep. 3, 20080;338(1-2):14-20. doi: 10.1016/j.jim.2008.06.004. Epub Jul. 2, 20083.
Xie et al., Discovery and development of plasma kallikrein inhibitors for multiple diseases. Eur J Med Chem. Mar. 1, 20205;190:112137(1-14). doi: 10.1016/j.ejmech.2020.112137. Epub Feb. 1, 20200.

(56) References Cited

OTHER PUBLICATIONS

Yang et al., Increased complement factor H with decreased factor B determined by proteomic differential displays as a biomarker of tai chi chuan exercise. Clin Chem. Jan. 2010;56(1):127-31. doi: 10.1373/clinchem.2009.126615. Epub Nov. 2, 2009.

[No Author Listed], Hereditary Angioedema (HAE) Guidelines 2010. Homepage of The Japanese Association of Complement Research. 2010. https://square.umin.ac.jp/compl/common/images/diseaseinformation/hae/HAEGuideline2010.pdf [last accessed Nov. 8, 2023]. 5 pages.

[No Author Listed], United States Court of Appeals for the Federal Circuit. *Erfindergemeinschaft Uropep GbR v. Eli Lilly and Company*. Appeal from the United States District Court for the Eastern District of Texas in No. 2:15-cv-01202-WCB, Circuit Judge William C. Bryson. Aug. 25, 2017. 83 pages.

Banerji et al., Effect of Lanadelumab Compared With Placebo on Prevention of Hereditary Angioedema Attacks: A Randomized Clinical Trial. JAMA. Nov. 27, 2018;320(20):2108-2121. doi: 10.1001/jama.2018.16773. Erratum in: JAMA. Apr. 23, 2019;321(16):1636.

Cozma et al., P46: Mass spectrometry based screening for hereditary angioedema disease. Allergy Asthma Clin Immunol. Aug. 13, 2019;15(Suppl 4):45. p. 39.

Kolker, D., Antibodies and the written description requirement of 35 U.S.C.112(a). USPTO Biotechnology Chemical Pharmaceutical Customer Partnership Meeting. Sep. 17, 2020, 36 pages.

Zeerleder et al., Hereditary and acquired C1-inhibitor-dependent angioedema: from pathophysiology to treatment. Ann Med. 2016;48(4):256-67. doi: 10.3109/07853890.2016.1162909. Epub Mar. 26, 2016.

* cited by examiner

LATERAL FLOW IMMUNOASSAY FOR MEASURING FUNCTIONAL C1-ESTERASE INHIBITOR (C1-INH) IN PLASMA SAMPLES

RELATED APPLICATIONS

This application claims the benefit under 35 U.S.C. § 119 (e) of U.S. provisional application No. 62/833,235, filed on Apr. 12, 2019, and U.S. provisional application No. 62/930,615, filed on Nov. 5, 2019 the entire contents of each is incorporated herein by reference.

BACKGROUND

C1-esterase inhibitor (also known as C1-inhibitor or C1-INH) is a protease inhibitor belonging to the serpin superfamily. Its main function is the inhibition of the complement system to prevent spontaneous activation. C1-INH is also an endogenous inhibitor for plasma kallikrein (pKal). Autosomal dominant mutation in C1-INH leads to hereditary angioedema (HAE), including types I and II HAE.

The currently available assays used to assess C1-INH functional level measure the inhibition of C1s of the complement cascade by C1-INH, utilizing either a chromogenic assay or a complex ELISA method. The chromogenic assay is generally considered preferable but both methods have limitations. The chromogenic assay is more likely to have an occasional false positive while the complex ELISA has a negative predictive value of only 62%.

It is of interest to develop newer assays and/or platforms for measuring functional C1-INH involved in the HAE disease pathology.

SUMMARY

Provided herein are devices and methods for detecting functional C1-INH (fC1-INH) in a qualitative and/or quantitative manner that is rapid and cost-effective. Detecting fC1-INH, in some embodiments, is achieved using a device configured for detecting and/or quantifying fC1-INH via a lateral flow immunoassay (LFA).

Accordingly, one aspect of the present disclosure provides a device for detecting and/or quantifying functional C1-esterase inhibitor (fC1-INH), the device comprising (i) a conjugate pad comprising a first zone and a second zone, on which a first agent and a second agent are immobilized, respectively, and (ii) a membrane, which is in communication with the conjugate pad, wherein the membrane comprises a third zone, on which a third agent is immobilized. The first agent can be a functional C1 inhibitor (fC1-INH) binding agent or a C1 inhibitor (C1-INH) binding agent. The second agent and the third agent are one of a functional C1 inhibitor (fC1-INH) binding agent, a C1 inhibitor (C1-INH) binding agent, and a capture agent. The first agent, the second agent, and the third agents are different from each other. One of the fC1-INH binding agent, the C1-INH binding agent, and the capture agent is conjugated to a detectable label, and one of the fC1-INH binding agent and the C1-INH binding agent is conjugated to a docking agent. The detectable label and the docking agent are conjugated to a different agent. The conjugate pad further comprises a fourth zone for placing a biological sample, which flows through the device in the order of the first zone, the second zone, and the third zone. In some instances, the fourth zone for placing the biological sample may overlap with the second zone, on which the fC1-INH binding agent may be located.

In some embodiments, the first agent, the second agent, and the third agent are the C1-INH binding agent, the fC1-INH binding agent, and the capture agent, respectively. In other embodiments, the first agent, the second agent, and the third agent are the fC1-INH binding agent, the C1-INH binding agent, and the capture agent, respectively.

In some examples, the first agent is conjugated to a detectable label, the second agent is conjugated to a docking agent. In other examples, the first agent is conjugated to a docking agent, the second agent is conjugated to a detectable label.

In some embodiments, the fC1-INH binding agent can be an active form of Factor XII (FXIIa). Alternatively or in addition, the C1-INH binding agent can be an antibody that binds C1-INH. Further, the docking agent and the capture agent can be members of a receptor-ligand pair. For example, the receptor-ligand pair can comprise biotin and avidin (e.g., streptavidin or polystreptavidin).

In some embodiments, the detectable label may be europium, colloidal gold, phycoerythrin, fluorescein, rhodamine, green fluorescent protein, quantum dot, and chromophore. In some embodiments, the detectable label is europium. In some instances, the detectable label may be attached to latex particles.

In one example, the first agent is the C1-INH binding agent located at the first zone, the second agent is the fC1-INH binding agent located at the second zone, and the third agent is the capture agent located at the third zone. The C1-INH binding agent may an antibody binding to C1-INH, which may be conjugated to a detectable label as disclosed herein. Alternatively or in addition, the fC1-INH binding agent may be FXIIa, which may be conjugated to a docking agent (e.g., biotin). Further, the capture agent can be an avidin, such as streptavidin or polystreptavidin.

In some embodiments, the device further comprises an absorbent pad in communication with the membrane. The absorbent pad and the conjugate pad may be separated by the membrane. Alternatively or in addition, the device may further comprise a support member, on which the conjugate pad, the membrane, and/or the absorbent pad is mounted.

Further, the device may also comprise a housing. In some embodiments, the housing may comprise a first opening to form a buffer port, a second opening to form a sample port, and a third opening to form a test window. The sample port can be located between the buffer port and the test window. In some examples, the buffer port may align with the first zone, on which the C1-INH binding agent is located. In some examples, the sample port may align with the second zone, on which the fC1-INH binding agent is located. In some examples, the test window aligns with the third zone, on which the capture agent is located.

In another aspect, the present disclosure provides methods for detecting and/or quantifying functional C1-esterase inhibitor (fC1-INH) in a sample using any of the LFA devices disclosed herein. Such a method may comprise: (i) placing a sample in the sample port of the device described herein, (ii) placing a buffer in the buffer port in the device, wherein the buffer flows in the direction from the first zone to the third zone; (iii) examining a signal at the test window in the device, and (iv) determining presence or measuring the level of fC1-INH in the sample based on presence or intensity of the signal at the test window. In some embodiments, step (ii) is performed at least at least 5 minutes after step (i). The fC1-INH binding agent can be immobilized at the second zone, which may align with the sample port.

Also provided herein are methods for detecting and/or quantifying functional C1-esterase inhibitor (fC1-INH) in a sample, the method comprising (i) contacting a sample with an fC1-INH binding agent, a C1-INH binding agent, and a capture agent to form a complex, wherein one of the fC1-INH binding agent and the C1-INH agent is conjugated to a docking agent, which binds the capture agent, and wherein one of the fC1-INH binding agent, the C1-INH agent, and the capture agent is conjugated to a detectable label, the detectable label and the docking agent being conjugated to a different agent; and (ii) detecting a signal released from the detectable label in the complex; wherein presence of the signal released from the detectable label in the complex indicates presence of fC1-INH in the sample. Any of the fC1-INH binding agent, the C1-INH binding agent, the docking agent, the detectable label, and the capture agent as disclosed herein can be used in the methods disclosed herein.

In some embodiments, step (i) can be performed by (a) incubating the sample with the fC1-INH binding agent for at least 5 minutes, and (b) contacting the sample with the C1-INH binding agent and the capture agent. In other embodiments, step (i) is performed by (a) incubating the sample with the fC1-INH binding agent for at least 5 minutes to form a first complex, (b) contacting the first complex with the C1-INH binding agent to form a second complex, and (c) contacting the second complex with the capture agent to form the complex, and wherein the capture agent is immobilized on a support member.

In any of the assay methods disclosed herein, the sample to be analyzed can be a biological sample obtained from a subject, for example, a serum sample, a plasma sample, or a blood sample (e.g., whole blood). In some embodiments, the subject can be a human patient suspected of having or at risk for a fC1-INH deficiency-mediated disorder, which includes, but is not limited to, hereditary angioedema (HAE), acquired angioedema (AAE), and a C1-INH related immune disease. In some embodiments, the subject has a symptom of HAE. In some embodiments, the HAE is type I HAE or type II HAE. In other embodiments, the subject has no symptom of HAE, has no history of a symptom of HAE, or no history of HAE. In some embodiments, the subject is resistant to an anti-histamine therapy, a corticosteroid therapy, or both.

The details of several embodiments of the devices and methods described herein are set forth in the accompanying Figures and the Detailed Description. Other features, objects, and advantages of the devices and methods described herein will be apparent from the description and from the claims.

DETAILED DESCRIPTION OF THE DRAWINGS

Various aspects and embodiments will be described with reference to the following figures. The figures are not necessarily drawn to scale.

FIG. 1 is a schematic depiction of an exemplary lateral flow assay (LFA) device 100 for detecting and/or quantifying functional C1-esterase inhibitor (fC1-INH). The LFA device 100 comprises a conjugate pad 200, a membrane 300, and optionally an absorbent pad 400, and a support member 500, in accordance with some embodiments of the technology described herein.

FIG. 2 is a schematic depiction of an exemplary LFA device 100 showing exemplary sizes of each components and exemplary sizes of overlap between two adjacent components, in accordance with some embodiments of the technology described herein.

FIG. 3A is a schematic depiction of a top view of an exemplary LFA device 100 for detecting and/or quantifying fC1-INH. The LFA device 100 comprises a conjugate pad 200, which comprises a first zone 210 and a second zone 220, and a membrane 300 comprising a third zone 230, in accordance with some embodiments of the technology described herein.

FIG. 3B is a schematic depiction of a top view of an exemplary LFA device 100 for detecting and/or quantifying fC1-INH. The LFA device 100 comprises a conjugate pad 200, which comprises a first zone 210 that overlaps with a fifth zone 250 for placing a sample and a second zone 220 that overlaps with a fourth zone 240 for placing a buffer, and a membrane 300 comprising a third zone 230, in accordance with some embodiments of the technology described herein.

FIG. 4 is a schematic depiction of a top view of an exemplary LFA device 100 for detecting and/or quantifying fC1-INH. The LFA device 100 further comprises a housing 600, forming a buffer port 610, a sample port 620, and a test window 630, in accordance with some embodiments of the technology described herein. A first zone 210, a second zone 220, a third zone 230, a conjugate pad 200, a membrane 300, and an absorbent pad 400 are also indicated.

Figure 17:
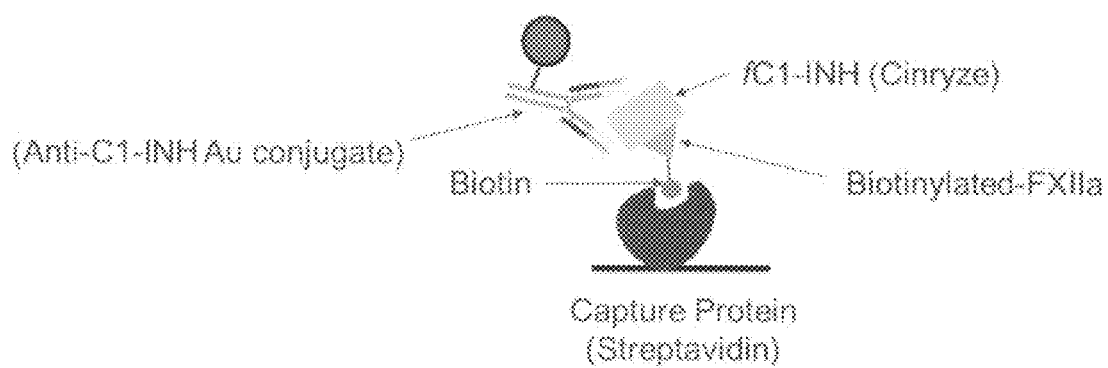

FIG. 17 is a schematic of exemplary methods described herein. A capture protein, such as streptavidin, interacts with its pair (e.g., biotin) conjugated to a capture agent (e.g., biotinylated FXIIa) which binds to functional C1-INH (fC1-INH, CINRYZE®). Bound fC1-INH is detected using a detection agent, such as an anti-C1-INH antibody conjugated to gold particles (anti-C1-INH Au conjugate).

DETAILED DESCRIPTION

The present disclosure is based, at least in part, on the development of lateral flow assay (LFA) methods and devices for measuring functional C1-esterase inhibitor (fC1-INH).

The LFA methods and devices are designed for specifically detecting presence of fC1-INH and/or measuring the level of fC1-INH in, e.g., a biological sample. Presence and/or the level of fC1-INH is often indicative of status of diseases associated with biological pathways in which C1-INH plays a role. As such, the LFA methods and devices would be particularly useful in diagnosis and prognosis of diseases mediated by C1-INH deficiency, for example, diseases mediated by the plasma kallikrein pathway (e.g., diseases such as hereditary angioedema) since fC1-INH is an inhibitor of the pKal pathway.

As used herein, "functional C1-INH" or "fC1-INH" refers to the C1-INH protein in the form that is capable of binding to a protein factor, to which C1-INH binds in nature and exerts its biological activity. Such a protein factor includes, but is not limited to, C1s, Factor XIIa (FXIIa), and plasma kallikrein (pKal). Detection of this subpopulation of fC1-INH is particularly helpful in assessing functional levels of C1-INH in diseases such as HAE.

HAE is a very rare and potentially life-threatening genetic condition that occurs in about 1 in 10,000 to 1 in 50,000 people. Symptoms include edema (swelling) in various parts of the body, including hands, feet, face and airway (throat). Patients often suffer excruciating abdominal pain, nausea, and vomiting caused by swelling in the intestinal wall. Swelling of the airway or throat is particularly dangerous; it can cause death by asphyxiation. The three specific blood tests required to confirm HAE Types I & II are C1INH antigen, fC1INH and C4. Many diagnostic assays use outdated technologies and are not rapid or standardized or available throughout the world.

The rapid and sensitive LFA methods and devices disclosed herein can be performed in a physician's office lab for rapid diagnosis of HAE (e.g., Type I & II) based on fC1INH levels. Such methods and devices would result in low cost consumables reimbursed by health insurance, high level of confidence in quantitative results, case of data interpretation by physicians, and/or low level of need for confirmatory analysis. Such a rapid analysis to diagnose Type I or II HAE in the physician's office can expand screening for HAE and identify new HAE patients more quickly. Currently, global diagnosis rate for HAE is only 40%; therefore, undiagnosed patients have high unmet need. Rapid test availability on common device platforms could expand recognition of HAE. Further, the rapid test for fC1INH disclosed herein can help in monitoring the HAE disease progression or response to therapeutics in a timely fashion in clinical settings.

The LFA methods and devices disclosed herein involve a first binding agent specific to fC1-INH (a fC1-INH binding agent), a second binding agent specific to C1-INH (specific to functional C1-INH, non-functional C1-INH, or both), and capture agent. Either the fC1-INH binding agent or the C1-INH binding agent can be conjugated with a docking agent capable of binding to the capture agent. One of the fC1-INH binding agent, the C1-INH binding agent, and the capture agent can be conjugated with a detectable label. Accordingly, fC1-INH in a sample (e.g., a biological sample) can form a complex with the fC1-INH binding agent and the C1-INH binding agent. Such a complex can bound to the capture agent via interaction between the capture agent and the docking agent conjugated to one of the C1-INH binding agent and the fC1-INH binding agent. Upon detection of a signal (e.g., presence or intensity) released from the detectable label, presence or the level of fC1-INH in the sample can be determined and/or quantified based on standards tested along with. For example, Cinryze®, purified human plasma derived CHINH, at different levels can be used as standards to generate a standard curve to extrapolate and determine levels of fC1INH in the sample as measured by any of the methods disclosed herein. The intensity of the signal released from the detectable label can be quantified to U/ml of fCH1INH in the sample based on the standards, and is indicative of the level of fC1-INH in the sample.

I. Components for Use in the Lateral Flow Assay (LFA)

The LFA methods and devices disclosed herein involve (i) a fC1-INH binding agent, (ii) a C1-INH binding agent, one of which is conjugated to a docking agent, and (iii) a capture agent, which binds the docking agent. One of (i)-(iii) is conjugated to a detectable label.

(a) fC1-INH Binding Agent

A fC1-INH binding agent is a molecule (e.g., a protein or a fragment thereof that binds fC1-INH) that specifically binds a functional C1-INH. A molecule is said to exhibit "specific binding" if it reacts more frequently, more rapidly, with greater duration and/or with greater affinity with a particular target (e.g., those disclosed herein) than it does with alternative targets, which can be an altered form of the particular target. For example, a molecule that specifically binds fC1-INH would react more frequently, more rapidly, with greater duration and/or with greater affinity to fC1-INH as compared with an alternative target, such as non-functional C1-INH. "Specific binding" or "preferential binding" does not necessarily require (although it can include) exclusive binding.

In some instances, a protein or polypeptide capable of binding to fC1-INH in nature, or the binding fragment thereof, may be used as the fC1-INH binding agent. In some examples, the fC1-INH binding agent is FXII, for example, the active form of FXII (FXIIa). Factor XII is a serum glycoprotein that participates in the initiation of blood coagulation, fibrinolysis, and the generation of bradykinin and angiotensin. Prekallikrein is cleaved by Factor XII to form kallikrein, which then activates Factor XII resulting in the formation of Factor XIIa and Factor XII fragments (Factor XIIf) ("*Histidine-rich glycoprotein binds factor XIIa with high affinity and inhibits contact-initiated coagulation*" Macquarrie, et al., *Blood* 117:4134-4141 2011). C1 inhibitor (C1-INH) has been shown to be an important plasma inhibitor of both Factor XIIa and Factor XIIf ("*Effect of negatively charged activating compounds on inactivation of factor XIIa by C1 inhibitor*" Pixley, et al., *Arch Biochem Biophys* 256 (2): 490-8 1987).

FXII proteins, including precursor forms, mature forms, and active forms thereof, were well known in the art. For example, the precursor protein sequence of human Factor XII and the active form thereof are provided under the GenBank Accession Number: NP_000496.2. FXII proteins of other species, e.g., non-human mammals, were also known in the art. Their structure information can be found in the art, for example, identified from publically available gene database, using the human FXII sequence as a query.

"Active" or "functional" Factor XII refers to a Factor XII polypeptide or Factor XII polypeptide fragment that retains a biological activity similar to, but may not be necessarily identical to, the naturally occurring Factor XII counterpart, including mature forms. In some embodiments, an active or functional Factor XII is a Factor XII polypeptide or Factor XII polypeptide fragment that binds to fC1-INH. In some embodiments, active or functional Factor XII is a Factor XIIa polypeptide or a Factor XIIa polypeptide fragment that binds to fC1-INH. In some embodiments, active or functional Factor XII is a Factor XIIf polypeptide or a Factor XIIf polypeptide fragment that binds to fC1-INH.

In other examples, the fC1-INH binding agent is plasma kallikrein (pKal), for example, the catalytic fragment of a naturally-occurring pKal protein. Plasma kallikrein is a serine protease component of the contact system (Sainz I. M. et al., Thromb Haemost 98, 77-83, 2007). The contact system is activated by either factor XIIa upon exposure to foreign or negatively charged surfaces or on endothelial cell surfaces by prolylcarboxypeptidases (Sainz I. M. et al., Thromb Haemost 98, 77-83, 2007). Activation of plasma kallikrein amplifies intrinsic coagulation via its feedback activation of factor XII and enhances inflammation via the production of the proinflammatory nonapeptide bradykinin. As the primary kininogenase in the circulation, plasma kallikrein is largely responsible for the generation of bradykinin in the vasculature.

pKal proteins are well known in the art. Exemplary plasma kallikrein sequences can include human (Accession Number: NP_000883.2), mouse (Accession Number: NP_032481.1), or rat (Accession Number: NP_036857.2) plasma kallikrein amino acid sequences.

"Active" or "functional" plasma kallikrein refers to a plasma kallikrein polypeptide or plasma kallikrein polypeptide fragment that retains a biological activity (e.g., protease activity) similar to, but may not be necessarily identical to, the naturally occurring plasma kallikrein counterpart, including mature forms. In some embodiments, an active or functional plasma kallikrein is a plasma kallikrein polypeptide or plasma kallikrein polypeptide fragment that binds to fC1-INH.

In yet other examples, the fC1-INH binding agent disclosed herein can be C1s and C1r, or active/functional fragments thereof. C1s and C1r are activated homologous serine proteases of the first component of complement (C1). Both C1s and C1r can form a complex with C1-INH. Arlaud et al., (1993) Methods Enzymol. 223, 61-82. C1s is the modular serine protease, which executes the catalytic function of the C1 complex. C1r is an enzyme that activates C1s to its active form, by proteolytic cleavage.

C1s and C1r proteins are also well known in the art. For example, the precursor protein sequence of human C1s is provided under GenBank Accession Number: NP_001725.1 and the human C1r is provided under GenBank Accession Number: NP_001724.4.

"Active" or "functional" C1s and C1r refers to C1s and C1r polypeptide fragment that retains a biological activity similar to, but may not be necessarily identical to, the naturally occurring C1s and C1r counterparts, including mature forms, respectively. In some embodiments, an active or functional C1s or C1r fragment is the portion of a C1s polypeptide or C1s polypeptide that binds to fC1-INH.

Any of the fC1-INH binding agents may be produced via recombinant technology, or isolated from a suitable natural source.

(b) C1-INH Binding Agent

The C1-INH binding agent for use in the LFA methods and devices disclosed herein can be any molecule (e.g., proteins or polypeptides) capable of binding to C1-INH. In some instances, the C1-INH binding agent is specific to fC1-INH. In other instances, the C1-INH binding agent cross-reacts with both functional and non-functional C1-INH.

The C1-INH binding agent may be an antibody that binds C1-INH. As used herein, the term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab and sFab fragments, F (ab')$_2$, Fd fragments, Fv fragments, scFv, and domain antibodies (dAb) fragments (de Wildt et al., *Eur J Immunol.* 1996; 26 (3): 629-39)) as well as complete antibodies. An antibody can have the structural features of IgA, IgG, IgE, IgD, IgM (as well as subtypes thereof).

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) *Sequences of Proteins of Immunological Interest, Fifth Edition, U.S. Department of Health and Human Services*, NIH Publication No. 91-3242, and Chothia, C. et al., (1987) *J. Mol. Biol.* 196:901-917. Kabat definitions are used herein. Each VH and VL is typically composed of three CDRs and four FRs, arranged from amino-terminus to carboxy-terminus in the following order: FR1, CDR1, FR2, CDR2, FR3, CDR3, FR4.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are interconnected by, e.g., disulfide bonds. In IgGs, the heavy chain constant region includes three immunoglobulin domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system. The light chains of the immunoglobulin may be of a kappa or lambda chain. In one embodiment, the antibody is glycosylated. An antibody can be functional for antibody-dependent cytotoxicity and/or complement-mediated cytotoxicity.

In some embodiments, the antibody that binds C1-INH may specifically bind to C1-INH, for example, an epitope of fC1-INH or an epitope shared by fC1-INH and non-functional C1-INH. An antibody that "specifically binds" to an antigen or an epitope is a term well understood in the art, and methods to determine such specific binding are also well known in the art. An antibody is said to exhibit "specific binding" if it reacts or associates more frequently, more rapidly, with greater duration and/or with greater affinity with a particular target antigen than it does with alternative targets. An antibody "specifically binds" to a target antigen or epitope if it binds with greater affinity, avidity, more readily, and/or with greater duration than it binds to other substances. For example, an antibody that specifically (or preferentially) binds to an antigen (e.g., C1-INH) or an antigenic epitope therein is an antibody that binds this target antigen with greater affinity, avidity, more readily, and/or with greater duration than it binds to other antigens or other epitopes in the same antigen. It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding. In some examples, an antibody that "specifically binds" to a target antigen or an epitope thereof may not bind to other antigens or other epitopes in the same antigen.

The antibody binding to C1-INH for use in the LFA methods and devices disclosed herein may have a suitable binding affinity for C1-INH or a suitable epitope thereof. As used herein, "binding affinity" refers to the apparent association constant or KA. The KA is the reciprocal of the dissociation constant (KD). The antibody described herein may have a binding affinity (KD) of at least $10^{-5}$, $10^{-6}$, $10^{-7}$, $10^{-8}$, $10^{-9}$, $10^{-10}$ M, or lower. An increased binding affinity corresponds to a decreased KD. Higher affinity binding of an antibody for a first antigen relative to a second antigen can be indicated by a higher KA (or a smaller numerical value KD) for binding the first antigen than the KA (or numerical value KD) for binding the second antigen. In such cases, the antibody has specificity for the first antigen relative to the second antigen. Differences in binding affinity (e.g., for specificity or other comparisons) can be at least 1.5, 2, 3, 4, 5, 10, 15, 20, 30, 40, 50, 60, 70, 80, 90, 100, 500, 1000, 10,000 or 105 fold. Binding affinity (or binding specificity) can be determined by conventional methods.

The antibody binding to C1-INH may be a full-length antibody. Alternatively, the antibody is an antigen-binding fragment of a full length antibody. The term "antigen-binding fragment" of a full length antibody refers to one or more fragments of a full-length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F (ab')$_2$ fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). Sec, e.g., U.S. Pat. Nos. 5,260,203, 4,946,778, and 4,881,175; Bird et al., (1988) *Science* 242:423-426; and Huston et al., (1988) *Proc. Natl. Acad. Sci. USA* 85:5879-5883. Antibody fragments can be obtained using any appropriate technique including conventional techniques known to those with skill in the art.

Any of the antibodies binding to C1-INH as described herein can be either monoclonal or polyclonal. A "monoclonal antibody" refers to a homogenous antibody population and a "polyclonal antibody" refers to a heterogeneous antibody population. These two terms do not limit the source of an antibody or the manner in which it is made.

The antibody binding to C1-INH can be made by any methods known in the art. See, for example, Harlow and Lane, (1998) Antibodies: A Laboratory Manual, Cold Spring Harbor Laboratory, New York. In some embodiments, antibodies specific to C1-INH (e.g., human C1-INH) can be made by the conventional hybridoma technology. In other embodiments, antibodies specific to C1-INH can be isolated from antibody libraries following conventional antibody library screening technology.

In some embodiments, the antibody is an antibody that specifically binds to human C1-INH. In some embodiments, the antibodies are monoclonal antibodies that specifically bind to human C1-INH. In some embodiments, the antibodies are mouse monoclonal antibodies that specifically bind to human C1-INH, such as antibody clone MM06 or MM03 (also referred to as 10995-MM06 and 10995-MM03, respectively, from Sino Biological Inc.). In some embodiments, the antibodies are polyclonal antibodies that specifically bind to human C1-INH. In some embodiments, the antibodies are rabbit polyclonal antibodies that specifically bind to human C1-INH, such as antibody clone RP01 or RP02 (also referred to as 10995-RP01 and 10995-RP02, respectively, from Sino Biological Inc.). In some embodiments, the antibody is RP02.

(c) Docking-Capture Agents

One of the fC1-INH binding agent and the C1-INH binding agent is conjugated with a docketing agent, which is capable of binding to the capture agent also used in the LFA methods and devices as disclosed herein. In one embodiment, the docking agent is conjugated to the fC1-INH binding agent (e.g., FXIIa). In other embodiments, the docking agent can be conjugated to C1-INH (e.g., an antibody binding to C1-INH).

The docking agent and capture agent are members of a receptor-ligand pair, which refers to any pair of molecules capable of binding to each other to form a complex. In one example, the docking agent and capture agent are biotin and avidin, respectively, or vice versa. For example, the docking agent may be biotin, and the capture agent may be streptavidin or polystreptavidin.

(d) Detectable Label

One of the fC1-INH binding agent, the C1-INH binding agent, and the capture agent for use in the LFA methods and devices as disclosed herein can be conjugated to a detectable label. In some embodiments, the fC1-INH binding agent is conjugated to the detectable label. In other embodiments, the C1-INH binding agent is conjugated to the detectable label. Alternatively, the capture agent is conjugated to the detectable label.

As used herein, a "detectable label" refers to any molecule that is capable of releasing a detectable signal, either directly or in directly. In some embodiments, the detectable label can be a fluorophore (e.g., fluorescein). As used herein, the term "fluorophore" (also referred to as "fluorescent label" or "fluorescent dye") refers to moieties that absorb light energy at a defined excitation wavelength and emit light energy at a different wavelength.

Examples of fluorophores include, without limitation, xanthene derivatives (e.g., fluorescein, rhodamine, Oregon green, eosin and Texas red), cyanine derivatives (e.g., cyanine, indocarbocyanine, oxacarbocyanine, thiacarbocyanine and merocyanine), naphthalene derivatives (e.g., dansyl and prodan derivatives), coumarin derivatives, oxadiazole derivatives (e.g., pyridyloxazole, nitrobenzoxadiazole and benzoxadiazole), pyrene derivatives (e.g., cascade blue), oxazine derivatives (e.g., Nile red, Nile blue, cresyl violet and oxazine 170), acridine derivatives (e.g., proflavin, acridine orange and acridine yellow), arylmethine derivatives (e.g., auramine, crystal violet and malachite green), tetrapyrrole derivatives (e.g., porphin, phthalocyanine and bilirubin), or fluorescent proteins (e.g., green fluorescent protein).

In some embodiments, the detectable label is phycoerythrin.

In some embodiments, the detectable label is a chromophore (e.g., anthracene). In some embodiments, the detectable label is a semiconductor particle (e.g., a quantum dot). In some embodiments, the detectable label is attached to semiconductor particles (e.g., quantum dots). In some embodiments, the detectable label is europium. In some embodiments, the detectable label is colloidal gold. In some embodiments, the detectable label is attached to gold particles. In some embodiments, the detectable label is attached to red gold particles. In some embodiments, the detectable label is attached to latex particles. In some embodiments, the C1-INH binding agent is antibody RP02 conjugated to europium. In some embodiments, the C1-INH binding agent is antibody RP02 conjugated to gold particles. In some embodiments, the C1-INH binding agent is antibody RP02 conjugated to red gold particles. In some embodiments, the C1-INH binding agent is antibody RP02 conjugated to latex particles.

II. LFA Devices

In some aspects, the present disclosure provides a lateral flow assay (LFA) device for measuring fC1-INH in a sample containing such. Reference is now made to FIGS. 1-4, which illustrate pictorially various embodiments of exemplary LFA devices described herein.

Figure 1:
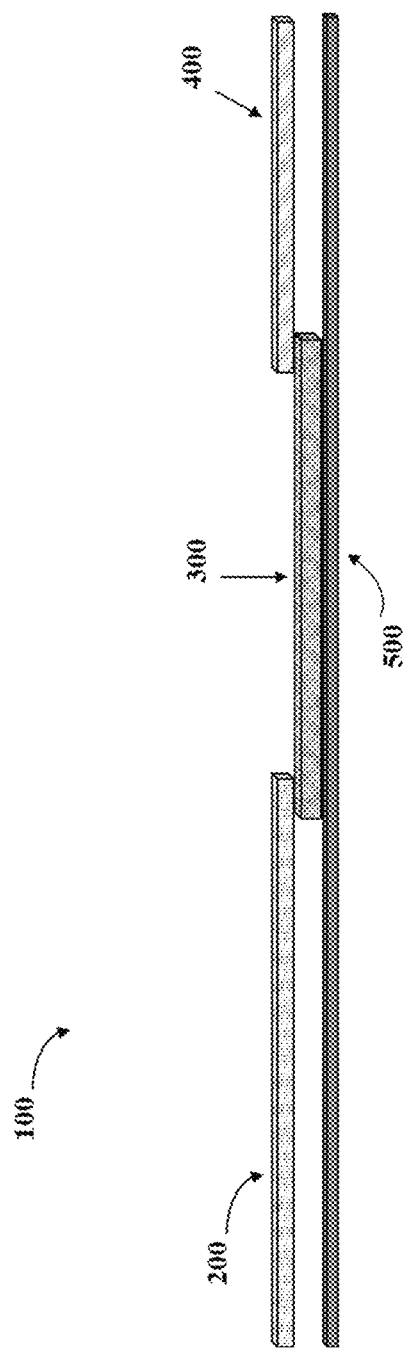

As shown in FIG. 1, the device 100, in some embodiments, comprises a conjugate pad 200, a membrane 300, and optionally an absorbent pad 400 and a support member 500, on which the conjugate pad 200, the membrane 300, and optionally the absorbent pad 400 are mounted.

Figure 2:
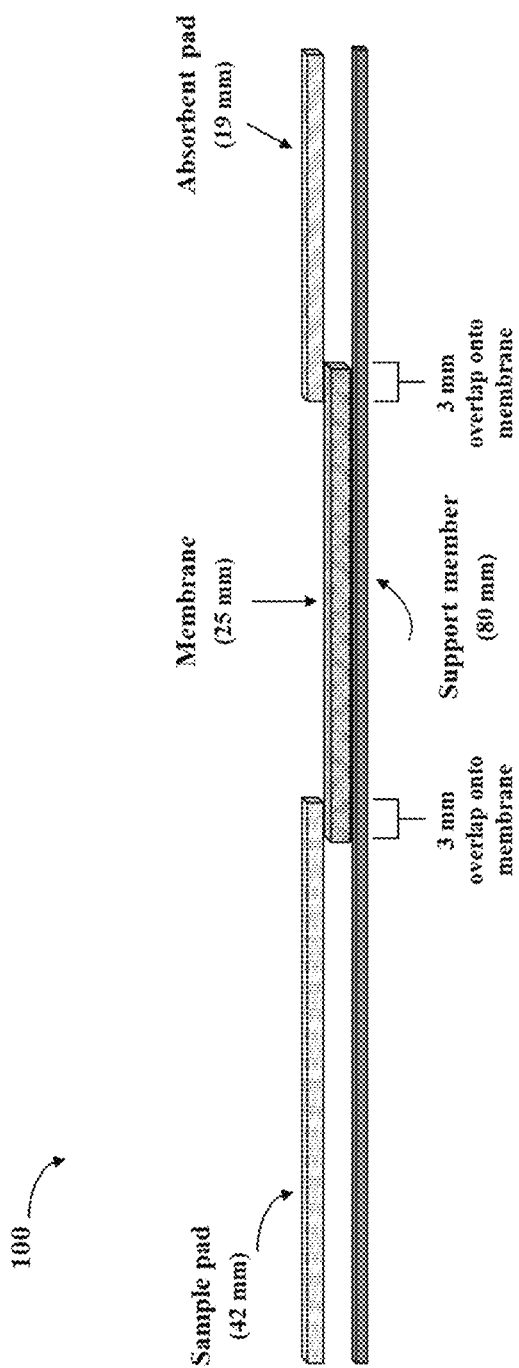

The conjugate pad 200 is in communication with the membrane 300, either directly or via a linker. When the device contains the absorbent pad 400, the conjugate pad 200 and the absorbent pad 400 are separated by the membrane 300, which is in communication with the absorbent pad 400, either directly or indirectly. In some embodiments, the conjugate pad 200 overlaps with the membrane 300, e.g., by 2-6 mm, such as 3 mm as shown in FIG. 2. Alternatively or in addition, the membrane 300 overlaps with the absorbent pad 400 by, e.g., 2-6 mm, such as 3 mm as shown in FIG. 2.

The specific characteristics and dimensions of the conjugate pad 200, the membrane 300, the absorbent pad 400, and the support member 500 can be modified as necessary to achieve desired results. As shown in FIG. 2, in some embodiments, the support membrane has a length of 80 mm, which is the combined length of the conjugate pad (42 mm), membrane (25 mm), and absorbent pad (19 mm) subtracted by the overlap of the sample pad and absorbent pad onto the membrane (3 mm, 3 mm).

Figure 3A:
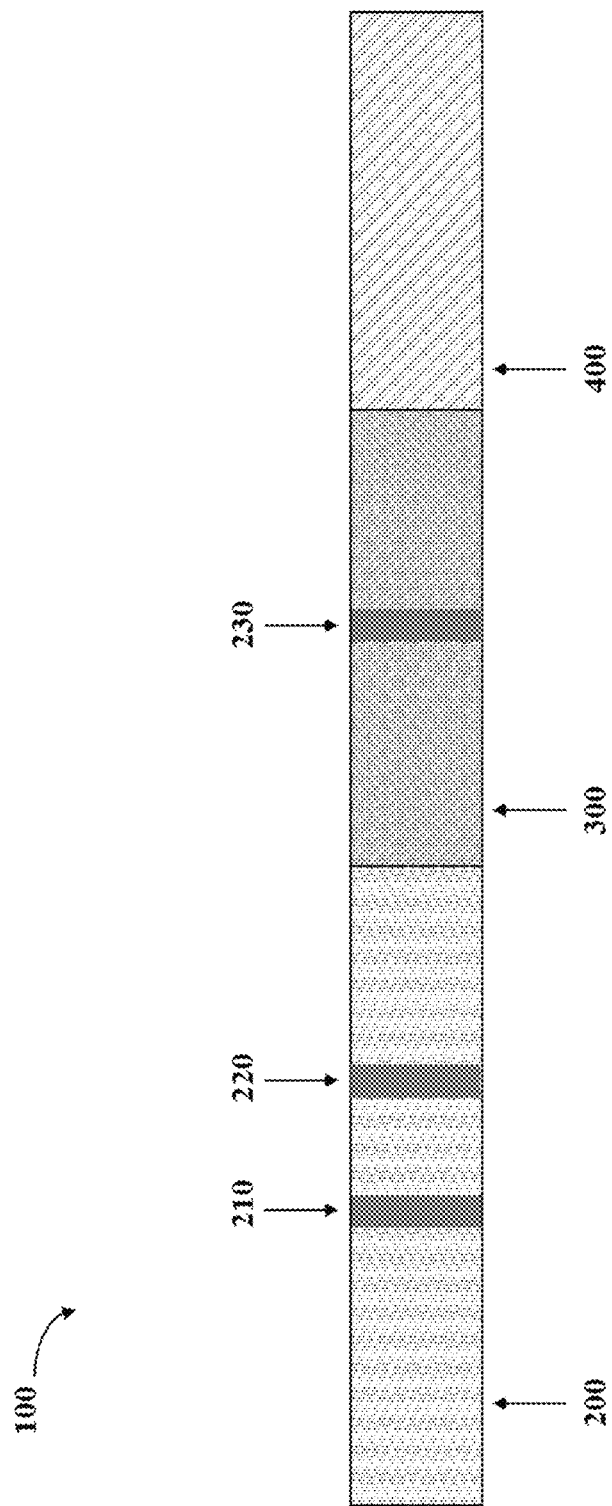
Figure 3B:
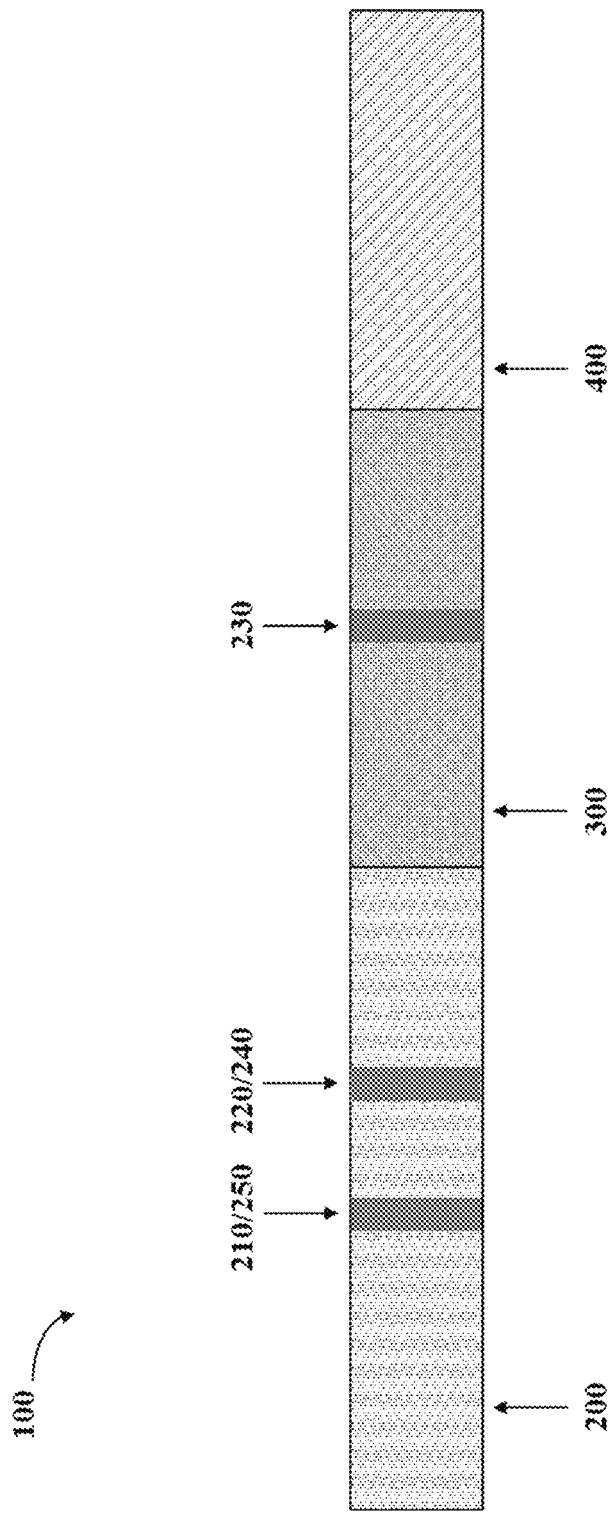

As shown in FIG. 3A, a top view of device 100, the device may comprise various zones (210, 220, 230) that are useful for, in some embodiments, immobilizing a fC1-INH binding agent, a C1-INH binding agent, and a capture agent as those described herein. In some embodiments, the device 100 comprises a first zone 210 and a second zone 220, which may be on the conjugate pad 200 and a third zone 230, which may be on the membrane 300.

Each of the fC1-INH binding agent, the C1-INH binding agent, and the capture agent may be immobilized on one of zones 210, 220, and 230 (which may be in any order). Any of these agents may be immobilized using any means known in the art. The agent may be immobilized on, or bound to, a surface of the conjugate pad 200 and/or the membrane 300, directly or indirectly. In some embodiments, the binding agent is immobilized to a surface via a covalent bond. In some embodiments, the binding agent is immobilized to a surface via a non-covalent bond. In some embodiments, the binding agent is immobilized to a surface via a linker. Examples of linkers, include, but are not limited to, carbon-containing chains, polyethylene glycol (PEG), nucleic acids, monosaccharide units, biotin, avidin, and peptides.

In some embodiments, a fC1-INH binding agent such as FXIIa is immobilized on the first zone 210. The fC1-INH binding agent may be conjugated to a docking agent such as biotin. A C1-INH binding agent such as an antibody binding to C1-INH may be immobilized on the second zone 220. The C1-INH binding agent may be conjugated to a detectable label such as those disclosed herein. A capture agent such as avidin (e.g., streptavidin) may be immobilized on the third zone 230.

In some embodiments, a fC1-INH binding agent such as FXIIa is immobilized on the first zone 210. The fC1-INH binding agent may be conjugated to a detectable label as those described herein. A C1-INH binding agent such as an antibody binding to C1-INH may be immobilized on the second zone 220. The C1-INH binding agent may be conjugated to a docking agent such as biotin. A capture agent such as avidin (e.g., streptavidin) may be immobilized on the third zone 230.

In some embodiments, a C1-INH binding agent such as an antibody binding to C1-INH can be immobilized on the first zone 210. The C1-INH binding agent may be conjugated to a docking agent such as biotin. A fC1-INH binding agent such as FXIIa may be immobilized on the second zone 220. The fC1-INH binding agent may be conjugated to a detectable label such as those described herein. A capture agent such as avidin (e.g., streptavidin) can be immobilized on the third zone 230.

In some embodiments, a C1-INH binding agent such as an antibody binding to C1-INH can be immobilized on the first zone 210. The C1-INH binding agent may be conjugated to a detectable label such as those described herein. A fC1-INH binding agent such as FXIIa may be immobilized on the second zone 220. The fC1-INH binding agent may be conjugated to a docking agent such as biotin. A capture agent such as avidin (e.g., streptavidin) can be immobilized on the third zone 230.

In some embodiments, a fC1-INH binding agent such as FXIIa is immobilized on the first zone 210. The fC1-INH binding agent may be conjugated to a docking agent such as biotin. A capture agent such as avidin (e.g., streptavidin) may be immobilized on the second zone 220. The capture agent may be conjugated to a detectable label such as those disclosed herein. A C1-INH binding agent such as an antibody binding to C1-INH may be immobilized on the third zone 230.

In some embodiments, a fC1-INH binding agent such as FXIIa is immobilized on the first zone 210. The fC1-INH binding agent may be conjugated to a detectable label such as those described herein. A capture agent such as avidin (e.g., streptavidin) may be immobilized on the second zone 220. A C1-INH binding agent such as an antibody binding to C1-INH may be immobilized on the third zone 230. The C1-INH binding agent may be conjugated to a docking agent such as biotin.

In some embodiments, a C1-INH binding agent such as an antibody binding to C1-INH may be immobilized on the first zone 210. The C1-INH binding agent may be conjugated to a docking agent such as biotin. A capture agent such as avidin (e.g., streptavidin) may be immobilized on the second zone 220. The capture agent may be conjugated to a detectable label such as those disclosed herein. A fC1-INH binding agent such as FXIIa may be immobilized on the third zone 230.

In some embodiments, a C1-INH binding agent such as an antibody binding to C1-INH may be immobilized on the first zone 210. The C1-INH binding agent may be conjugated to a detectable label such as those described herein. A capture agent such as avidin (e.g., streptavidin) may be immobilized on the second zone 220. A fC1-INH binding agent such as FXIIa may be immobilized on the third zone 230. The fC1-INH binding agent may be conjugated to a docking agent such as biotin.

Any of the LFA devices disclosed herein may further comprise the $4^{th}$ zone 240, which may be for placing a sample such as those described herein, and optionally the $5^{th}$ zone 250, which may be for placing a buffer solution.

The $5^{th}$ zone 250 may be located at one end of the device such that when a buffer solution is placed on the $5^{th}$ zone 250, the buffer solution can flow through the device from the $1^{st}$ zone 210 toward the $3^{rd}$ zone 230. In some examples, the $5^{th}$ zone 250 may overlap with the $1^{st}$ zone 210. See FIG. 3B. In this instance, a C1-INH binding agent such as an antibody binding to the C1-INH may be immobilized on the $1^{st}$ zone 210, which overlaps with the $5^{th}$ zone 250. The C1-INH binding agent may be conjugated to a detectable label.

Alternatively or in addition, the $4^{th}$ zone 240 may be located between the $5^{th}$ zone 250 and the $2^{nd}$ zone 220. In some instances, the $4^{th}$ zone 240 and the $2^{nd}$ zone 220 may overlap. See FIG. 3B. A fC1-INH binding agent such as FXIIa, which may be conjugated to a docking agent such as biotin, may be immobilized on the $2^{nd}$ zone 220.

Figure 4:
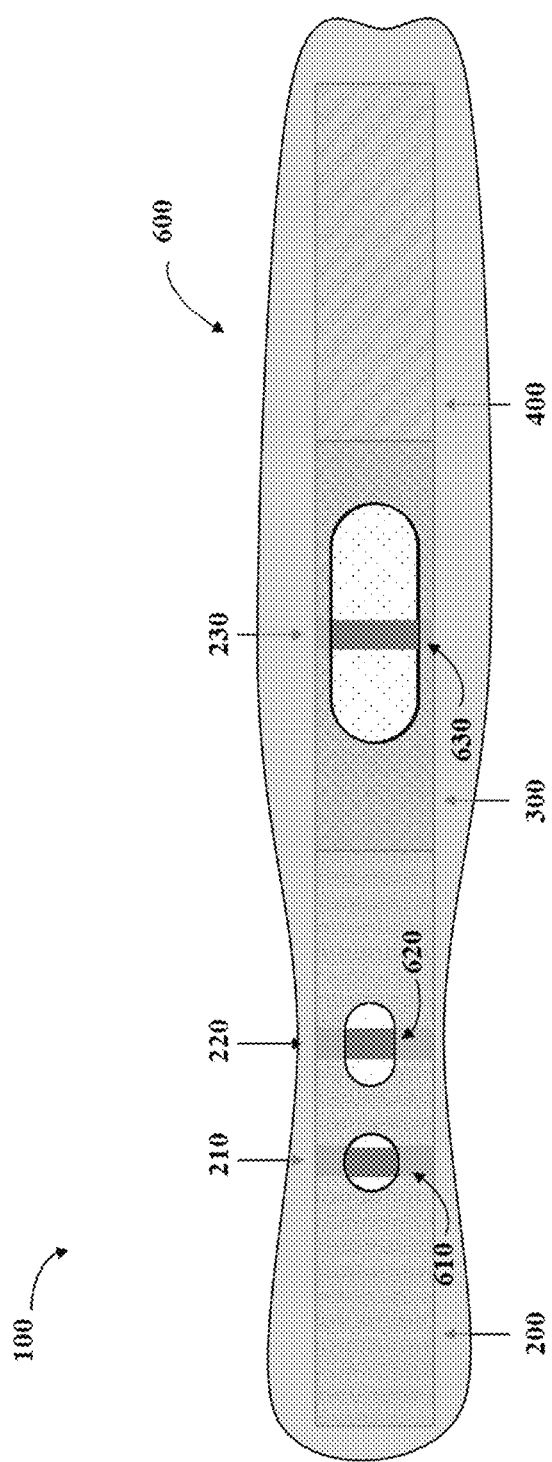
Figure 5:
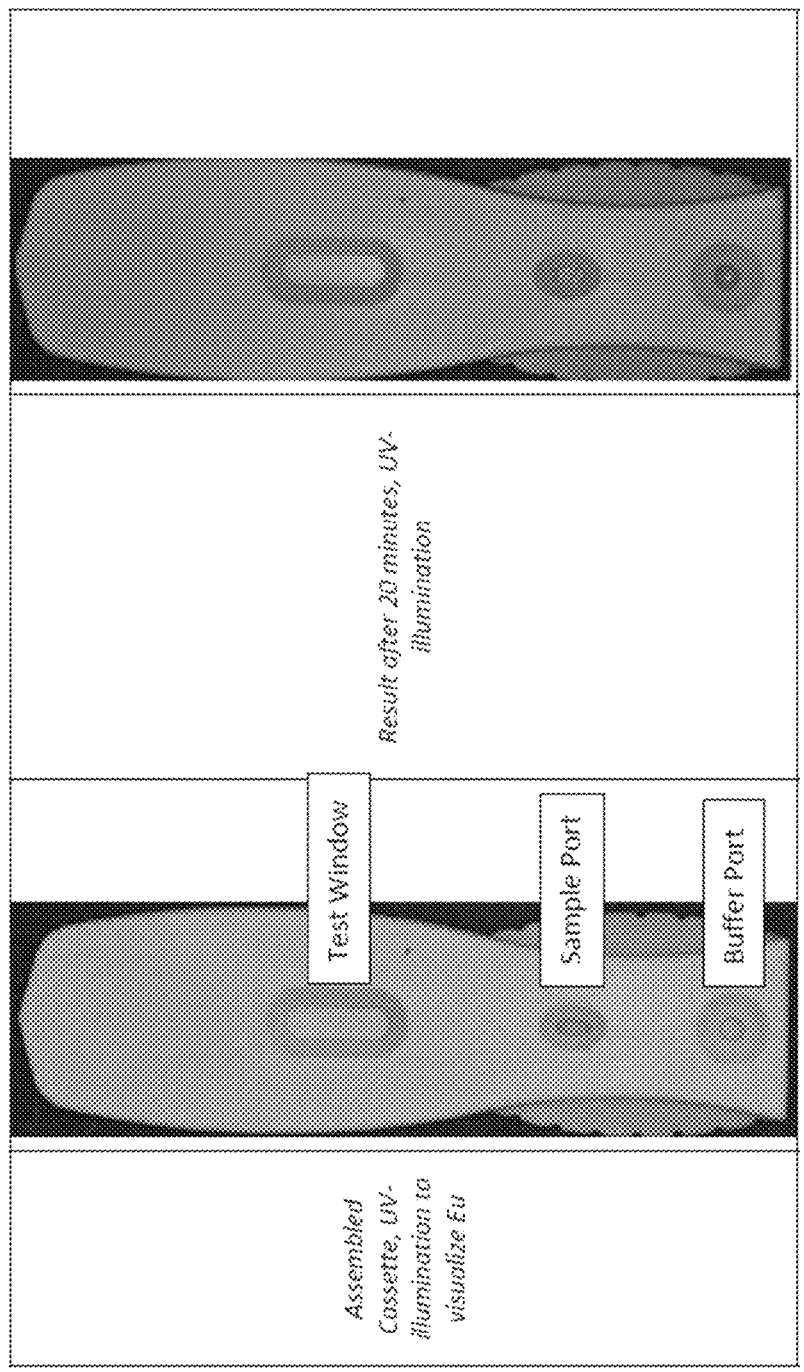
FIG. 5 is an image of an exemplary LFA device, in accordance with some embodiments of the technology described herein.

As shown in FIG. 4, the device 100, in some embodiments, may further comprise a housing 600, which may be removable. An image of a device as described herein in a housing is shown in FIG. 5. The housing 600 may be and configured to expose at least a portion of the conjugate pad 200 and the membrane 300 of the device 100. In some embodiments, the housing 600 comprises a first opening to form a buffer port 610, which may align with the first zone 210. The housing 600 may further comprise a second opening to form a sample port 620, which may align with the second zone 220. Further, the housing 600 may comprise a third opening to form a test window 630, which may align with the third zone 230.

In some embodiments, a C1-INH binding agent such as an antibody binding to C1-INH is immobilized on the $1^{st}$ zone 210, which aligns with the buffer port 610. FIG. 4. The C1-INH binding agent may be conjugated to a detectable label such as those described herein. A fC1-INH binding agent such as FXIIa may be immobilized on the $2^{nd}$ zone 220, which may align with the sample port 620. The fC1-INH binding agent may be conjugated to a docking agent such as biotin. A capture agent such as avidin (e.g., streptavidin) may be immobilized on the $3^{rd}$ zone 230, which may align with the test window 630.

In some examples, a sample can be placed in the sample port 620, allowing binding of fC1-INH therein with FXIIa-biotin conjugate. A buffer solution can be placed in the buffer port 610, allowing migration of the C1-INH binding agent on the $1^{st}$ zone 210 toward the $2^{nd}$ zone 220 along with the buffer solution. When the C1-INH binding agent is in contact with the fC1-INH-FXIIa complex at the $2^{nd}$ zone 220, a complex of C1-INH binding agent/fC1-INH/FXIIa-biotin is formed. This complex would migrate toward the $3^{rd}$ zone 230 along with the buffer solution and be captured at the $3^{rd}$ zone 230 via the interaction between biotin and streptavidin at the $3^{rd}$ zone 230. A signal released from the detectable label conjugated to the C1-INH binding agent at the $3^{rd}$ zone 230, which align with the test window 630, can be measured, which indicates presence or level of fC1-INH in the sample.

Alternatively or in addition, the housing 600 may be clear to facilitate visualization of the sample port 610 and/or the buffer port 620 and/or the test window 630. In some embodiments, a portion of the housing is clear. In some embodiments, the whole housing 600 is clear.

The housing 600, in some embodiments, comprises a label to facilitate identification of a sample or a result. In some embodiments, the housing 600 comprises one or more labels to facilitate identification of a result in a test window 630. In some embodiments, the one or more labels identify a sample result.

It should be appreciated that various embodiments of the device, including the multiple components in the device (e.g., the conjugate pad, the membrane, the absorbent pad, and the support member) as described herein may be formed with suitable materials, e.g., with any suitable conjugate pad, with any suitable membrane, with any suitable absorbent pad, with any suitable support member, with any suitable binding agent, and with any suitable combination thereof.

For example, the membrane 300 in an LFA device as disclosed herein may be any suitable membrane including, but is not limited to, a nitrocellulose membrane, a nylon membrane, a cellulose membrane, a polyvinylidine fluoride membrane, a polycarbonate membrane, a polypropylene membrane, a polyethylene membrane, a polytetrafluoroethylene membrane, and a poly-paraphenylene terephthalamide membrane. In some embodiments, the membrane is a nitrocellulose membrane.

Any suitable support member may be used in a device described herein. In some embodiments, the support member comprises metal. In some embodiments, the support member comprises plastic. In some embodiments, the support member comprises plastic selected from the group consisting of styrene, polycarbonate, polypropylene, polyethylene, and polyvinyl chloride.

Any suitable pad may be used as the conjugate pad in a device described herein. In some embodiments, the conjugate pad comprises cellulose or glass fiber. In some embodiments, the absorbent pad comprises cellulose or glass fiber.

A device provided herein may further comprise a sample pad. In some embodiments, the sample pad comprises cellulose or glass fiber.

It should be appreciated that various embodiments of the present invention may be formed with one or more of the above-described features. The above aspects and features of the invention may be employed in any suitable combination as the present invention is not limited in this respect. It should also be appreciated that the drawings illustrate various components and features which may be incorporated into various embodiments of the present invention. For simplification, some of the drawings may illustrate more than one optional feature or component. However, the present invention is not limited to the specific embodiments disclosed in the drawings. It should be recognized that the present invention encompasses embodiments which may include only a portion of the components illustrated in any one drawing figure, and/or may also encompass embodiments combining components illustrated in different figures.

III. Measurement of Functional C1-INH

Also provided herein are methods for detecting and/or quantifying functional C1-esterase inhibitor (fC1-INH) in a sample. The assay methods disclosed herein involve the use of a fC1-INH binding agent, a C1-INH binding agent, and a capture agent, which are all disclosed herein. One of the fC1-INH binding agent and the C1-INH agent is conjugated to a docking agent, which binds the capture agent. One of the fC1-INH binding agent, the C1-INH agent, and the capture agent is conjugated to a detectable label. The detectable label and the docking agent are conjugated to a different agent.

To perform the assay method disclosed herein, a sample suspected of containing fC1-INH can be brought in contact with the fC1-INH binding agent, the C1-INH binding agent, and the capture agent under conditions allowing for formation of a complex comprising the fC1-INH, the fC1-INH binding agent, the C1-INH binding agent, and the capture agent (via interaction with the docking agent conjugated to either the fC1-INH binding agent or the C1-INH binding agent). Presence or level of the fC1-INH in the sample can be detected and/or quantified by measuring a signal released from the detectable label, which can be in conjugation to any one of the fC1-INH binding agent, the C1-INH binding agent, and the capture agent.

In some examples, the sample and the fC1-INH binding agent (e.g., FXIIa) can be incubated first for a suitable period (e.g., at least 5 minutes, such as 5-10 minutes) to allow formation of a fC1-INH/FXIIa complex. The complex can then be incubated with a C1-INH binding agent such as an antibody binding to C1-INH to form a three-component complex, which can then be in contact with a capture agent that binds the docking agent conjugated to either the fC1-INH binding agent or the C1-INH binding agent. A signal released from the detectable label conjugated to one component in the final complex can be measured for determining presence/absence and/or level of fC1-INH in the sample.

Methods for detecting and/or quantifying fC1-INH provided herein, in some embodiments, comprise (i) contacting a sample with an fC1-INH binding agent, a C1-INH binding agent, and a capture agent to form a complex, wherein one of the fC1-INH binding agent and the C1-INH agent is conjugated to a docking agent, which binds the capture agent, and wherein one of the fC1-INH binding agent, the C1-INH agent, and the capture agent is conjugated to a detectable label, the detectable label and the docking agent being conjugated to a different agent; and (ii) detecting a signal released from the detectable label in the complex; wherein presence of the signal released from the detectable label in the complex indicates presence of fC1-INH in the sample.

Methods described herein encompass a capture agent immobilized on any suitable substrate in any suitable manner. Examples of substrates include, but are not limited to, beads, particles, slides, and multi-well plates. In some embodiments, the capture agent is bound covalently to the substrate. In some embodiments, the capture agent is bound non-covalently to the substrate. In some embodiments, the capture agent is bound indirectly to the substrate, e.g., through a linker.

In some embodiments, the assay methods disclosed herein can be carried out using any of the LFA devices disclosed herein. For example, a sample may be placed in the sample port 620 (FIG. 4) and a buffer solution may be placed in the buffer port 610. The sample port 620 may be aligned with the $2^{nd}$ zone 220. The buffer port 610 may be aligned with the $1^{st}$ zone 210. The buffer solution would flow from, e.g., the $1^{st}$ zone 210 toward the $2^{nd}$ zone 220 and the third zone 230, along with the sample and the fC1-INH binding agent, the C1-INH binding agent, and/or the capture agent immobilized on the $1^{st}$ zone 210 and the $2^{nd}$ zone 220. This allows for the contact of the sample with the fC1-INH binding agent, the C1-INH binding agent, and the capture agent when the buffer solution passes through the $1^{st}$ zone 210, the $2^{nd}$ zone 220, and the $3^{rd}$ zone 230, such that a complex comprising the fC1-INH in the sample, the fC1-INH binding agent, the C1-INH binding agent, and the capture agent can be formed. Presence or the level of fC1-INH in the sample can be determined by measuring a signal released from the detectable label conjugated to one component in the complex.

In one example, a method for detecting and/or quantifying fC1-INH with a LFA device comprising FXIIa-biotin and anti-C1-INH antibody conjugated to europium particles, e.g., a device configured as shown in FIG. 4, is described for illustration purposes only. In this example, anti-C1-INH antibody conjugated to europium particles functions as a C1-INH binding agent conjugated to a detection label, and the anti-C1-INH antibody conjugate is immobilized in the first zone 210. FXIIa conjugated to biotin functions as a fC1-INH binding agent conjugated to a docking agent, and FXIIa-biotin is immobilized in the second zone 220. To detect presence of fC1-INH in a sample, the sample is placed at the second zone 220 on the conjugate pad 200 via the sample port 620. When the sample contacts the FXIIa-biotin in the second zone 220, fC1-INH in the sample binds to FXIIa, thereby forming a FXIIa-biotin: fC1-INH complex.

As used herein, the term "contacts" refers to an exposure of a sample with one or more binding agents for a suitable period sufficient for the formation of a complex with fC1-INH and/or C1-INH in the sample, if any. In some embodiments, the sample and/or buffer contacts one or more binding agents via capillary action, in which a sample and/or buffer moves across a conjugate pad or a membrane.

A buffer may be placed at the first zone 210 on the conjugate pad 200 via the buffer port 610. The buffer may be placed at the first zone 210 any length of time after placing the sample at the second zone 220, e.g., the buffer may be placed at least 5 minutes after placing the sample in the device. The buffer solubilizes the anti-C1-INH antibody conjugate, and moves it along the conjugate pad 200 from the first zone 210 toward the membrane 300 via capillary action. When the buffer reaches the second zone 220, it contacts the FXIIa-biotin: fC1-INH complex, and the anti-C1-INH antibody conjugate in the buffer binds to fC1-INH in complex with FXIIa-biotin, thereby forming a "sandwich." In this example, the fC1-INH sandwich therefore comprises FXIIa conjugated to biotin bound to fC1-INH, which is bound by the anti-C1-INH antibody conjugated to europium particles.

The buffer comprising the fC1-INH sandwich continues to move up the conjugate pad 200 to the membrane 300, on which streptavidin is immobilized at the third zone 230 (e.g., a test line). In this example, streptavidin functions as the capture agent that binds to the docking agent, specifically biotin. When the buffer comes into contact with streptavidin at the third zone 230, biotin in the fC1-INH sandwich binds to streptavidin at the third zone 230, thereby capturing the fC1-INH sandwich. Presence of fC1-INH in the sample is then detected based on presence of signal from the europium particles at the third zone 230 via test window 630. Detection of the fC1-INH sandwich is not limited to detection via europium particles. For example, presence of fC1-INH may be detected via a detectable change in color or pH. If fC1-INH is absent in the sample, no fC1-INH sandwich is formed, and no signal is detected at the third zone 230.

After moving into the third zone 230, the sample continues to move up the membrane 300 into the absorbent pad 400, which acts as a wick to pull the sample upward, thus removing any background material from the third zone 230.

Methods provided herein encompass detecting and/or quantifying fC1-INH, or a lack thereof, in various samples. In some embodiments, the sample is a biological sample obtained from a subject. In some embodiments, the biological sample is a serum sample, a plasma sample, or a blood sample. In some embodiments, the sample is obtained from a subject suspected of having or at risk for a fC1-INH deficiency-mediated disorder (e.g., HAE).

In some embodiments, the biological sample is a blood sample, e.g., a whole blood, obtained from a subject. Whole blood comprises red blood cells, white blood cells, platelets, and blood plasma. In some embodiments, a blood sample may be collected from blood vessels (e.g., capillaries, veins, and arteries). In some embodiments, a blood sample may be obtained by a fingerstick that produces drop(s) of blood. In some embodiments, following obtaining the blood sample, the blood samples are handled at 2-8° C. For plasma or serum preparation, the plasma or serum may be prepared after blood collection by centrifugation. Plasma and serum samples may be stored at −80° C. prior to analysis.

In some embodiments, the methods and/or devices described herein may further comprise a control line. As will be understood by one of ordinary skill in the art, a control line may be used to ensure that the method and/or device is functioning as intended, e.g., detecting fC1-INH.

IV. Application of LFA Methods and Devices

Methods and devices described herein can be applied for evaluation of disease, e.g., diagnosis or prognosis of a disease. Evaluation may include identifying a subject as being at risk for or having a disease as described herein, e.g., a fC1-INH deficiency-mediated disorder. Evaluation may also include monitoring treatment of a disease, such as evaluating the effectiveness of a treatment for a fC1-INH deficiency-mediated disorder. Examples of fC1-INH deficiency-mediated disorders include, but are not limited to, hereditary angioedema (e.g., type I and/or type II HAE), acquired angioedema (e.g., type I and/or type II AAE), C1-INH deficiency related immune diseases (e.g., systemic lupus erythematosus (SLE), and C1-INH deficiency related cancers (e.g., lymphoma).

In some embodiments, the methods and devices used herein are used to evaluate whether a subject has or is risk for hereditary angioedema. In general, there are different types of hereditary angioedema, which exhibit similar inflammatory responses but differ in their etiology. For example, type 1 HAE is associated with functional but low levels of C1-INH, whereas type II HAE is associated with non-functional C1-INH that are present at normal concentrations.

A. Diagnosis

In some embodiments, the methods and devices described herein are used to determine the level of fC1-INH in a biological sample (e.g., a serum sample or a plasma sample or a blood sample) collected from a subject (e.g., a human patient suspected of having a fC1-INH deficiency-mediated disorder such as HAE). The fC1-INH level is then compared to a reference value to determine whether the subject has or is at risk for the fC1-INH deficiency-mediated disorder. The reference value can be a control level of fC1-INH capable of binding to a fC1-INH binding agent as described herein (e.g., FXIIa). In some embodiments, the control level is a level of fC1-INH in a control sample that is capable of binding to a fC1-INH binding agent. In some embodiments, a control sample is obtained from a healthy subject or population of healthy subjects. As used herein, a healthy subject is a subject that is apparently free of the fC1-INH deficiency-mediated disorder at the time the level of fC1-INH is measured or has no history of the disease.

The control level can also be a predetermined level. Such a predetermined level can represent the level of fC1-INH in a population of subjects that do not have or are not at risk for the fC1-INH deficiency-mediated disorder. The predetermined level can take a variety of forms. For example, it can be single cut-off value, such as a median or mean. In some embodiments, such a predetermined level can be established based upon comparative groups, such as where one defined group is known to have a target disease and another defined group is known to not have the target disease. Alternatively, the predetermined level can be a range, for example, a range representing the levels of fC1-INH in a control population within a predetermined percentile.

The control level as described herein can be determined by various methods. In some embodiments, the control level can be obtained by performing a known method. In some embodiments, the control level can be obtained by performing the same assay used for determining the level of fC1-INH in a sample from a subject. In some embodiments, the control level can be obtained by performing a method described herein. In some embodiments, the control level can be obtained with a device described herein. In some embodiments, the control level can be obtained from members of a control population and the results can be analyzed by, e.g., a computational program, to obtain the control level (a predetermined level) that represents the level of fC1-INH in the control population.

By comparing the level of fC1-INH capable of binding to a fC1-INH binding agent in a sample obtained from a subject to the reference value as described herein, it can be determined as to whether the subject has or is at risk for a fC1-INH deficiency-mediated disease (e.g., HAE). For example, if the level of fC1-INH that binds to a fC1-INH binding agent of the subject deviates from the reference value (e.g., reduced as compared to the reference value), the candidate subject might be identified as having or at risk for the fC1-INH deficiency-mediated disease, e.g., HAE. The assay disclosed herein can be used to predetermine a cutoff value representing fC1-INH in normal subjects. Such a cutoff value can be used for determining whether a subject has or is at risk for a fC1-INH deficiency-mediated disease (e.g., HAE). In some instances, the level of fC1-INH in a subject is lower than the cutoff value may indicate disease risk or occurrence.

As used herein, "a decreased level or a level below a reference value" means that the level of fC1-INH that binds to a fC1-INH binding agent is lower than a reference value, such as a pre-determined threshold or a level of fC1-INH that binds to a fC1-INH binding agent in a control sample.

An decreased level of fC1-INH that binds to a fC1-INH binding agent includes a fC1-INH level that is, for example, 50%, 60%, 70%, 80%, 90%, 100%, 150%, 200%, 300%, 400%, 500% or more lower than a reference value. A decreased level of fC1-INH that binds to a fC1-INH binding agent also includes decreasing a phenomenon from a non-zero state (e.g., some or detectable fC1-INH that binds to a fC1-INH binding agent in a sample) to a zero state (e.g., no or undetectable fC1-INH that binds to a fC1-INH binding agent in a sample).

In some embodiments, the subject is a human patient having a symptom of a fC1-INH deficiency-mediated disease, e.g., those disclosed herein such as HAE. For example, the subject has edema, swelling wherein said swelling is completely or predominantly peripheral; hives; redness, pain, and swelling in the absence of evidence of infection; non-histamine-mediated edema, recurrent attacks of swelling, or a combination thereof. In some embodiments, the subject has no symptom of a fC1-INH deficiency-mediated disease at the time the sample is collected, has no history of a symptom of a fC1-INH deficiency-mediated disease, or no history of a fC1-INH deficiency-mediated disease such as HAE. In some embodiments, the subject is resistant to an anti-histamine therapy, a corticosteroid therapy, or both.

Examples of fC1-INH deficiency-mediated diseases include, but are not limited to, non-histamine-dependent idiopathic angioedema, rheumatoid arthritis, Crohn's disease, lupus, Alzheimer's disease, septic shock, burn injury, brain ischemia/reperfusion injury, cerebral edema, diabetic retinopathy, diabetic nephropathy, macular edema, vasculitis, arterial or venous thrombosis, thrombosis associated with ventricular assist devices or stents, heparin-induced thrombocytopenia with thrombosis, thromboembolic disease, and coronary heart disease with unstable angina pectoris, edema, eye disease, gout, intestinal bowel disease, oral mucositis, neuropathic pain, inflammatory pain, spinal stenosis-degenerative spine disease, post-operative ileus, aortic aneurysm, osteoarthritis, hereditary angioedema, pulmonary embolism, stroke, head trauma or peri-tumor brain edema, sepsis, acute middle cerebral artery (MCA) ischemic event (stroke), restenosis (e.g., after angioplasty), systemic lupus erythematosis nephritis, an autoimmune disease, an inflammatory disease, a cardiovascular disease, a neurological disease, a disease associated with protein misfolding, a disease associated with angiogenesis, hypertensive nephropathy and diabetic nephropathy, allergic and respiratory diseases (e.g., anaphylaxis, asthma, chronic obstructive pulmonary disease, acute respiratory distress syndrome, cystic fibrosis, persistent, rhinitis) and tissue injuries (e.g., burn or chemical injury).

B. Evaluate Treatment Effectiveness

Methods and devices described herein can also be applied to evaluate the effectiveness of a treatment for a fC1-INH deficiency-mediated disease (e.g., HAE). For example, multiple biological samples (e.g., serum, plasma, or blood samples) can be collected from a subject to whom a treatment is performed either before and after the treatment or during the course of the treatment. The levels of fC1-INH can be measured by any method described herein. If the level of the fC1-INH increases after the treatment or over the course of the treatment (the level of fC1-INH in a later collected sample as compared to that in an earlier collected sample), remains the same or increases, it indicates that the treatment is effective.

If the subject is identified as not responsive to the treatment, a higher dose and/or frequency of dosage of the therapeutic agent are administered to the subject identified. In some embodiments, the dosage or frequency of dosage of the therapeutic agent is maintained, lowered, or ceased in a subject identified as responsive to the treatment or not in need of further treatment. Alternatively, a different treatment can be applied to the subject who is found as not responsive to the first treatment.

Therapeutic agents include, but are not limited to, kallikrein binding agents, bradykinin B2 receptor antagonists, C1-INH replacement agents, DX-2930, and DX88 (see, e.g., PCT Publication No. WO 2014/113701, which is incorporated herein by reference in its entirety).

EXAMPLES

In order that the devices and methods described herein may be more fully understood, the following examples are set forth. The examples described in this application are offered to illustrate the methods and compositions provided herein and are not to be construed in any way as limiting their scope.

Example 1: Preparation of a Lateral Flow Assay (LFA) Device for Detecting and/or Quantifying Functional C1-Esterase Inhibitor (fC1-INH)

Striping of Membranes

FRONTLINE HR™ (BioDot) was used to stripe membranes. Front lines were washed with 10 cycles of wash buffer (0.05% BIO-TERGE® (Stepan Company) in diH$_2$O), and aligned so that the test line was dispensed 11 mm from the bottom of the membrane. Front lines were emptied and primed with 0.5 mg/mL polystreptavidin in 10 mM phosphate, pH 7.3, 0.5% sucrose. Test lines of polystreptavidin were striped onto membranes (see, e.g., at a third zone 230 on a membrane 300 in FIG. 3A). Then, membranes were labeled and dried at 40° C. for 30 minutes. Front lines were washed with 10 cycles of wash buffer following striping. Components for striping membranes are shown in Table 1.

TABLE 1

Components for striping of membranes.

| Component | Grade | Vendor | Part Number | Amount per mL |
|---|---|---|---|---|
| 0.5M Sodium Phosphate, pH 7.3 | N/A | DCN | 10026 | Variable |
| Polystreptavidin | N/A | Biotez | PolyStrept R | |
| Sucrose | ACS | Sigma | S5500 | 5 mg |
| Water (diH2O) | ≥18M ohm | Thermo | ≥18M ohm | QS to final volume |

TABLE 1-continued

Components for striping of membranes.

| Component | Grade | Vendor | Part Number | Amount per mL |
|---|---|---|---|---|
| 0.05% BIO-TERGE ® | N/A | DCN | N/A | N/A |
| Membrane (25 mm × 300 mm) | CN95 | Sartorius | 1UN95ER1000025NTB | N/A |
| Frontline Striper | N/A | BioDot | XYZ 3210 | N/A |
| Large Foil Bag | IMPAK | 125MF518 | Large Foil Bag | Large Foil Bag |
| Desiccants, 0.5 g | IMPAK | 39SG03 | Desiccants, 0.5 g | Desiccants, 0.5 g |

Striping of Conjugate Pads

FRONTLINE HR™ (BioDot) was used to stripe anti-C1-INH Eu particle conjugates and FXIIa-biotin onto the conjugation pad (Ahlstrom). Prior to striping conjugate pads, anti-C1-INH Eu particle conjugates were diluted to 0.04% w/v into Eu Latex Diluent, and FXIIa-biotin was diluted to 2.4 µM in FXIIa-biotin Diluent. Then, front lines were washed with 10 cycles of wash buffer (0.05% BIO-TERGE® (Stepan Company) in diH$_2$O). Front lines were aligned so that the anti-C1-INH Eu particle conjugate was striped 15 mm from the bottom of the conjugate pad, and FXIIa-biotin conjugate was striped 8 mm from the top of the conjugate pad at a rate of 10 and 2.5 µL/cm, respectively. Positions of the anti-C1-INH Eu particle conjugate and FXIIa-biotin conjugate align with the buffer port and sample port in custom SLA housing cassettes, respectively.

Front lines were emptied and primed with either conjugate. Conjugates were striped onto the conjugate pads, which were then labeled and dried at 40° C. for 30 minutes. Conjugate pads were sealed and desiccated. Front lines were washed with 10 cycles of wash buffer following striping. Components for striping conjugate pads are shown in Table 2. Components for Eu Latex Diluent and FXIIa-biotin Diluent are shown in Table 3 and Table 4, respectively.

TABLE 2

Components for striping of conjugate pads

| Component | Grade | Vendor | Part Number |
|---|---|---|---|
| Conjugate Pad (42 mm × 300 mm) | Fiberglass | Ahlstrom | 8951 |
| Anti-C1-INH Eu Particles | N/A | DCN | Prepared as in NBR 715-001 |
| FXIIa-biotin | N/A | Enzyme Research Labs | HFXIIabiotin 3790 |
| FXIIa-biotin Diluent: 10 mM Tris pH 8, 0.1% Tween-20, 2% Casein, 10% Sucrose, 4% Trehalose, 0.25% Green Food Dye | N/A | DCN | N/A |
| Eu Latex Diluent: 10 mM Tris pH 8, 0.1% Tween-20, 2% Casein, 10% Sucrose, 4% Trehalose | N/A | DCN | N/A |
| Frontline Striper | N/A | BioDot | XYZ 3210 |
| Large Foil Bag | N/A | IMPAK | 125MF518 |
| Desiccants, 0.5 g | N/A | IMPAK | 39SG03 |

TABLE 3

Components for Eu Latex Diluent

| Component | Grade | Vendor | Part Number | Amount per mL |
|---|---|---|---|---|
| Tris-HCl | Reagent | Sigma | T3253 | N/A |
| 6% Casein in 50 mM Tris, pH 8,5, 7-Day Cure | N/A | DCN | Prepared as 21NOV21085M | N/A |
| Tween-20 | BioXtra | Sigma | P7949 | 10 µL |
| Sucrose | ACS | Sigma | S5500 | 100 mg |
| Trehalose | ACS | Fisher | BP2687100 | N/A |
| Water (diH2O) | ≥18M ohm | Thermo | ≥18M ohm | QS to final volume |

TABLE 4

Components for FXIIa-biotin Diluent

| Component | Grade | Vendor | Part Number | Amount per mL |
|---|---|---|---|---|
| Tris-HCl | Reagent | Sigma | T3253 | N/A |
| 6% Casein in 50 mM Tris, pH 8,5, 7-Day Cure | N/A | DCN | Prepared as 21NOV21085M | N/A |
| Tween-20 | BioXtra | Sigma | P7949 | 10 µL |
| Sucrose | ACS | Sigma | S5500 | 100 mg |
| Trehalose | ACS | Fisher | BP2687100 | N/A |
| Green Food Dye | Food Grade | Vons | N/A | 2.5 µL |
| Water (diH2O) | ≥18M ohm | Thermo | ≥18M ohm | QS to final volume |

Preparation of Anti-C1-INH Eu Particle Conjugate

To prepare the anti-C1-INH Eu particle conjugate, 0.1 mg of anti-C1-INH antibody was exchanged into 50 mM borate, pH 8 via ZEBA™ spin columns (Thermo Fisher) using the manufacture's protocol. The concentration of the antibody was determined by absorbance (A280, 1 mm, 1 OD=1.4 mg/mL). Stock latex was rotated for 10 minutes, and then sonicated for 10-15 seconds using a microtip sonicator (setting 25). Stock latex solution (10%) was diluted to 1% in 0.1 M MES, pH 6.5, and microfuged for 10 minutes at 17,000 g. Supernatant was removed, and the pellet was resuspended in 0.1 M MES, pH 6.5 with the volume of buffer being equal to the starting volume of latex. The resulting solution was sonicated, microfuged, and resuspended as previously described.

To prepare 15 mg/mL of EDC in 0.1 M MES buffer, EDC was allowed to equilibrate to room temperature, and weighted out. The EDC solution was prepared within 10 minutes of using in the preparation of anti-C1-INH Eu particle conjugates. EDC stock powder was desiccated and frozen at −20° C. for long term storage.

To prepare 50 mg/mL of sulfo-NHS in 0.1 M MES buffer, sulfo-NHS was allowed to equilibrate to room temperature, and weighted out. The sulfo-NHS solution was prepared within 10 minutes of using in the preparation of anti-C1-INH Eu particle conjugates. The sulfo-NHS solution was activated by incubation for 30 minutes on a shaker at 1000 rpm. The solution was microfuged for 8 minutes at 17,000 g. Pellets were resuspended in 50 mM borate buffer, vortexed, and sonicated. The volume of buffer was equal to the starting volume of latex solution (600 µL). The solution was then microfuged, resuspended in borate buffer (300 µL), vortexed, and sonicated as previously described. Activated particles were aliquoted into 50 µL/tube, and appropriate amounts of buffer and protein (e.g., 20 µg protein (i.e., antibody)) were added to obtain 20:1 mass to mass ratio of particles to protein. Tubes were vortexed immediately after the addition of buffer and protein.

Tubes were incubated for 2 hours at room temperature on a shaker at 1,000 rpm. Following incubation, 1 M ethanolamine at 10 µL/mL was added, and tubes were incubated for 30 minutes at room temperature on a shaker at 1,000 rpm. Tubes were microfuged for 10 minutes at 17,000 g, and pellets were resuspended into 1% casein 7-day cured and incubated overnight with shaking. Following the overnight incubation, tubes were microfuged, and pellets were resuspended into 1% casein 7-day cured, vortex, and sonicated. Particle conjugates were then striped onto conjugate pads as described herein. Components for anti-C1-INH Eu particle conjugates are shown in Table 5.

TABLE 5

Anti-C1-INH Eu particle conjugates

| Component | Grade | Vendor | Part Number | Amount per mL |
|---|---|---|---|---|
| Anti-C1-INH antibody | N/A | Shire | AbD28387.2 | 0.05 mg |
| Eu Latex Particles, 0.2 µm | N/A | Thermo | 93470520010150 | 1 mg |
| Conjugate Storage Diluent: 10 mM Tris pH 8, 1% Casein | DCN | DCN | N/A | 1 mL |
| 0.1M MES, pH 6.5 | N/A | DCN | N/A | N/A |
| 0.1M Borate, pH 8 | N/A | DCN | 10061 | N/A |
| Water (diH2O) | ≥18M ohm | Thermo | ≥18M ohm | QS to final volume |
| 6% Casein in 50 mM Tris, pH 8.5, 7-Day Cure | N/A | DCN | Prepared as 21NOV2108SM | N/A |
| EDC | N/A | Thermo | 22980 | N/A |
| NHS | N/A | Thermo | 24500 | N/A |
| Ethanolamine | N/A | TCI | A0297 | N/A |
| Scientific Centrifuge | N/A | Thermo | Legend XTR | N/A |
| Micro Plate Mixer | N/A | Scilogex | 82200004SX | N/A |
| Sonicator | N/A | Qsonica | Q55 | N/A |

Laminating Components onto Backing Card

To laminate components onto the 80 mm long backing card (DCN), the backing sticker was cut at 39 mm from bottom of card using a straightedge razor blade. The backing stickers were removed from the 39 mm position on the top of the card. The membrane was adhered to the card at 39 mm from the bottom of the card. The absorbent pad (Ahlstrom) was adhered to the top of the card so that the pad overlapped 3 mm with top of the membrane. The remaining backing stickers were removed, and the conjugate pad was adhered to the bottom of the card so that the pad overlapped 3 mm with bottom of the membrane. Components and component order are shown in Table 6 and Table 7, respectively.

TABLE 6

Card components

| Component | Material | Length (mm) | Location from bottom of strip (mm) |
|---|---|---|---|
| Membrane | Sartorius CN95 | 25 mm | 39 mm |
| Conjugate Pad | Ahlstrom 8951 | 42 mm | N/A |
| Wick Pad (Absorbent Pad) | Ahlstrom 243 | 19 mm | 61 mm |
| Backing Card (Support Membrane) | DCN P/N P12-651 | 80 mm | N/A |
| Location of Test Line | | | 11 mm (center) from bottom edge of membrane. 1 mm width in total. |
| Overall Strip Width | | | 5.0 mm |

TABLE 7

Lamination component order, orientation, and positions

| Order # | Component | Orientation | Position from bottom of Card | Overlap onto Membrane |
|---|---|---|---|---|
| 1 | Striped Membrane | Membrane side up, test line closest to bottom of card | 39 mm | N/A |
| 2 | Absorbent Pad | Smooth side down | 61 mm | 3 mm |
| 3 | Striped Conjugation Pad | Eu conjugate closest to bottom of card | N/A | 3 mm |

Preparing Test Strips

Cards were placed into the Kinematic Cutter (Kinematic), and cards were cut into 5.0 mm wide strips. Strips shorter than 5.0 mm or strips that had been marked in pen during striping were discarded. Cut strips were placed into foil bags with desiccant. Foil bags were sealed and stored in desiccated box until use.

Example 2: Use of LFA Device for Detecting Functional C1-Esterase Inhibitor (fC1-INH) in Plasma Samples from Patients To perform a lateral flow assay (LFA) for determining fC1-INH concentration, the test strips prepared as described in Example 1 above were placed into a custom stereolithography (SLA) cassette (see, e.g., FIG. 4). Standards and quality controls were prepared by spiking C1-INH reference standard (lot #TCP103, Shire, a Takeda Company) into C1-INH depleted human K3-EDTA plasma (prepared by Shire, a Takeda company). Control samples containing 0 mU/mL to 800 mU/mL of purified C1-INH were used to generate a calibration curve. Control samples were diluted 1:20 in C1-INH depleted media. The sample was added to the sample port and incubated for 5 minutes. Run buffer (30 µL) was added to the sample port, which allowed the sample to run onto the membrane and up to the test window. Run buffer (150 µL) was then added to the buffer port, and the cassette was incubated for an additional 20 minutes. The test strip was removed from the cassette, and the intensity of the test line area was measured using the Axxin AX-2X fluorescent reader (Axxin). An image of a test strip in a cassette is shown in FIG. 5. The measured intensity of the test line area was plotted against the C1-INH concentration to generate the calibration curve shown in FIG. 6, and gave a $R^2$ of 0.97.

Fifty normal K3-EDTA plasma samples were obtained commercially and fifty HAE plasma samples were used with patient consent from SAHARA, a Phase-III, randomized, double-blind, placebo-controlled, two-period, three-sequence, partial crossover study, that evaluated the efficacy and safety of subcutaneous administration of 2000 IU of C1 esterase inhibitor [Human] liquid for injection for the prevention of angioedema attacks in adolescents and adults with HAE.

Figure 6:
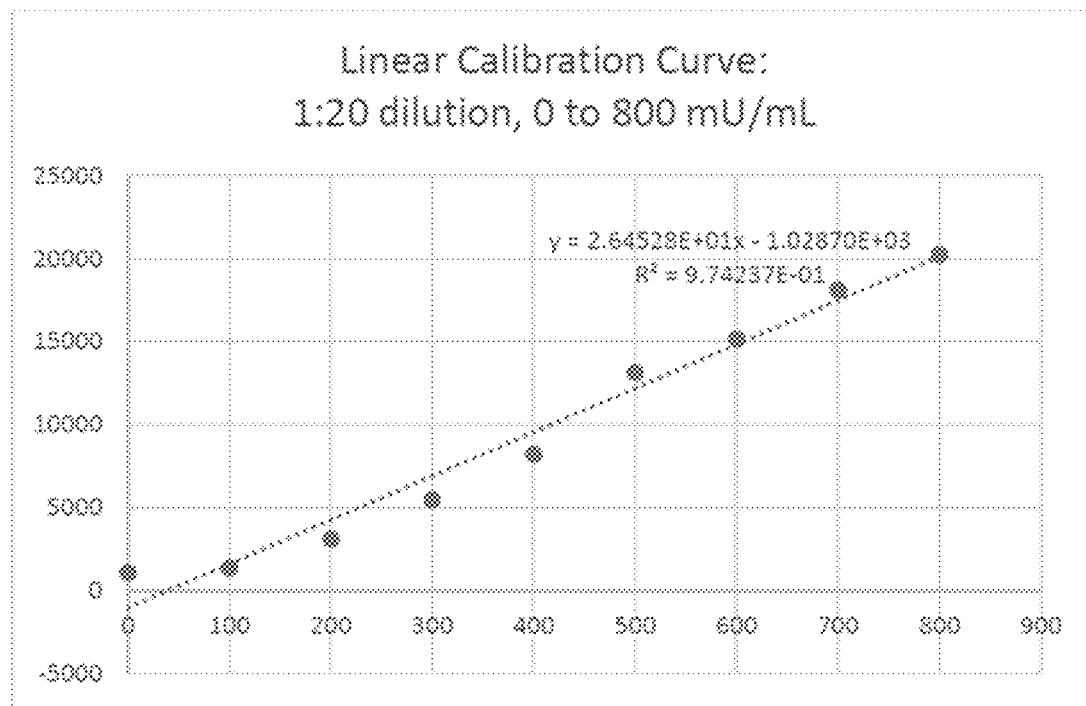
FIG. 6 is a graph showing a calibration curve generated from functional C1-esterase inhibitor (fC1-INH) diluted into C1-INH depleted plasma using the LFA device disclosed herein.

The calibration curve from FIG. 6 was then used to determine the fC1-INH concentration in plasma samples from the control subjects and subjects having hereditary angioedema (HAE). Briefly, plasma samples from the subjects were diluted 1:20 in C1-INH depleted plasma. The diluted plasma sample (20 µL) was added to the sample port, and incubated for 5 minutes. The fC1-INH concentrations determined using test strips were within 20% of concentration values determined by ELISA.

Figure 8:
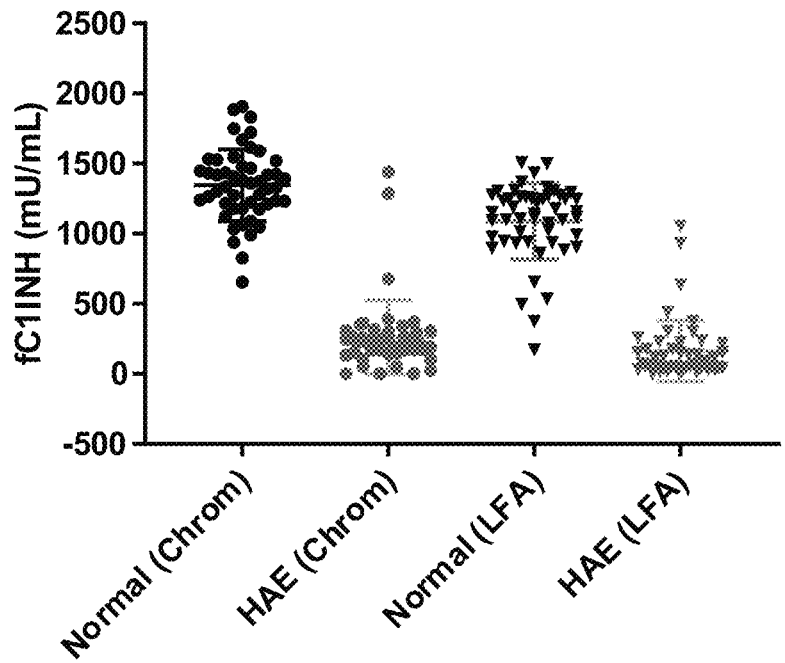
FIG. 8 is a graph showing the level of functional C1-INH in normal subjects (Normal) and subjects with hereditary angioedema (HAE) using a chromogenic assay (Chrom) or the LFA device (LFA) described herein.
Figure 9:
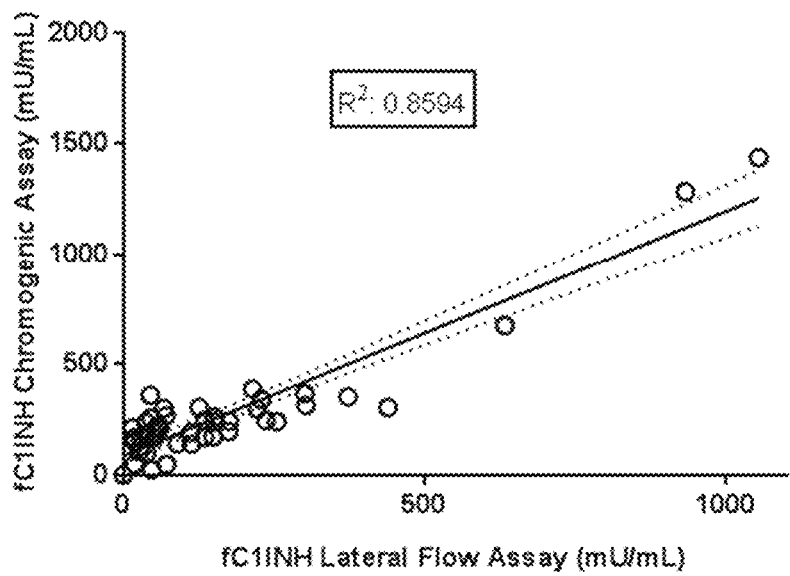
FIG. 9 is a graph showing the correlation between the level of functional C1-INH in subjects with hereditary angioedema (HAE) as determined by a chromogenic assay as compared to the LFA device described herein.

As shown in FIG. 8, C1-INH levels were lower in HAE subjects as compared to the healthy controls in both methods. The measured average C1-INH concentrations were 1345 and 1089 mU/mL for healthy controls and 275 and 163 mU/mL for HAE subjects in the Chromogenic and LFA methods, respectively (Table 8). The SEM and 95% confidence intervals for the measurements are provided in Table 8. C1-INH data for all HAE subjects obtained from the two methods correlated with each other with a $R^2$ pf 0.86, including two HAE subjects who had C1-INH concentrations in the healthy control range (FIG. 9). The average ratios between fC1INH measured normal controls and HAE subjects were 4.9 and 6.7 in chromogenic and LFA methods, respectively.

Figure 7:
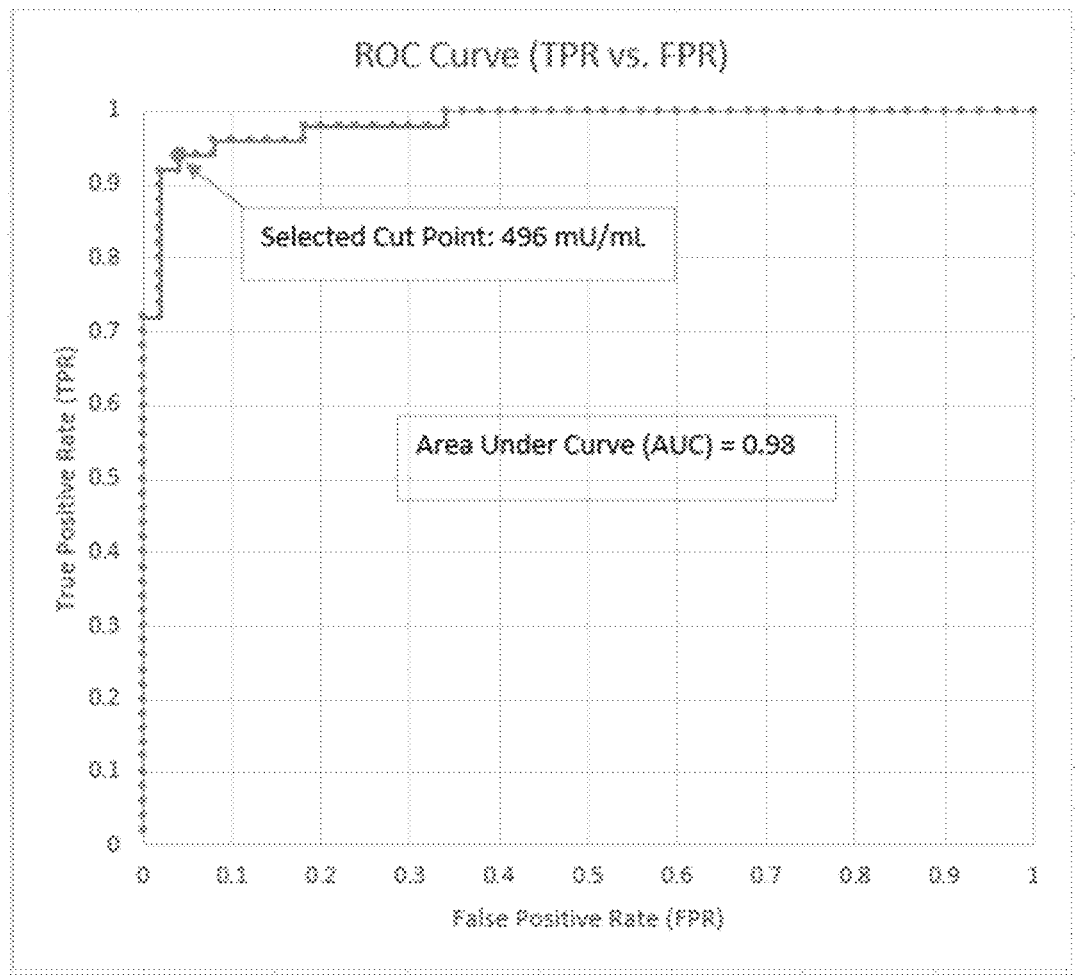
FIG. 7 is a graph of receiver operating curve (ROC) for diagnostic performance based on samples from control subjects and subjects with hereditary angioedema (HAE), using the LFA device disclosed herein.

Receiver operating curve (ROC) for diagnostic performance based on samples from control subjects and subjects with HAE was 0.98 indicating that the C1-IHN concentration determined by LFA accurately discriminated between control and HAE subjects (FIG. 7). The ROC curve indicated that a C1-INH cut point of 496 mU/mL yields a sensitivity (true positive rate) of 94% and specificity (false positive rate) of 96% (FIG. 7); the false negative and false positives are listed in Table 9.

As shown in Table 8 and FIGS. 8-9, results obtained using the LFA were compared to analysis using a chromogenic assay by ELISA. Briefly, the chromogenic method directly measures fC1-INH levels, involving C1s cleaving a synthetic substrate to form a color compound, where diminished color intensity demonstrates inhibition of C1s enzymatic activity. The chromogenic assay was qualified for precision, accuracy, linearity and upper and lower limits of quantitation. C1-INH protein (2000 IU of C1 esterase inhibitor [Human] liquid for injection, Shire, a Takeda Company) was used to prepare three quality controls as well as standard curve with ten standard points ranging from 1000-1.95 mU/mL. The highest and lowest points of standard curve were used as the anchor points. In brief, the K3-EDTA plasma samples and reference protein were pre-incubated with recombinant human complement component C1s protein (R&D Systems) for 30 minutes at room temperature (RT) in a polypropylene plate. The formed C1-INH and C1s complex was diluted 1:5 in assay buffer and mixed with substrate solution ((synthetic substrate with a thiobenzyl ester group, M-1300, Bachem) and 5,5'-Dithiobis(2-nitrobenzoic acid) (DTNB) #D-8000, Biosynth) and the reaction was allowed to incubate for 40 minutes at RT. Absorbance was recorded at 405 nm using SpectraMax M5 plate reader with SoftMax Pro software.

TABLE 8

Results that compare the Chromogenic Assay and LFA to determine fC1-INH concentration

| | | fC1INH measurement using Chromogenic Assay | fC1INH measurement using LFA |
|---|---|---|---|
| Normal Control Plasma Samples | Mean | 1345 mU/mL | 1089 mU/mL |
| | n | 50 | 50 |
| | SEM | 36 mU/mL | 38 mU/mL |
| | 95% Confidence Interval | 1272-1418 mU/mL | 1011-1166 mU/mL |
| HAE Plasma Samples | Mean | 275 mU/mL | 163 mU/mL |
| | n | 50 | 50 |
| | SEM | 39 mU/mL | 32 mU/mL |
| | 95% Confidence Interval | 196-354 mU/mL | 100-227 mU/mL |

TABLE 9

Results that show false positives and negatives of control and HAE samples.
LFA fC1-INH Cut Point = 496 mU/mL

| | HAE Samples | Normal Controls |
|---|---|---|
| LFA Positive for HAE | 47 | 2 |
| LFA Negative for HAE | 3 | 48 |

Taken together, these results demonstrate that similar fC1-INH concentrations were detected in patient plasma samples by LFA and ELISA (referred to as the chromogenic assay). Therefore, the LFA and test strips described herein may be an effective tool for identifying patients having HAE based on the level of fC1-INH in a plasma sample from the patient. The results obtained using the LFA described herein correlated with the results from the chromogenic assay for assessing fC1-INH.

The rapid and sensitive LFA methods and devices disclosed herein can be performed in a physician's office lab for rapid diagnosis of HAE (e.g., Type I & II) based on fC1INH levels. Such methods and devices may result in low cost consumables reimbursed by health insurance, high level of confidence in quantitative results, ease of data interpretation by physicians, and/or low level of need for confirmatory analysis. Such a rapid analysis to diagnose Type I or II HAE in the physician's office can expand screening for HAE and identify new HAE patients more quickly. Currently, global diagnosis rate for HAE is only 40%; therefore, undiagnosed patients have a high unmet need. Rapid test availability on common device platforms could expand recognition of HAE. Further, the rapid test for fC1INH disclosed herein can help in monitoring the HAE disease progression or response to therapeutics in a timely fashion in clinical settings.

REFERENCES

1. Maurer, M. et al. (2018) The international WAO/EAACI guideline for the management of hereditary angioedema—the 2017 revision and update. World Allergy Organization Journal
2. Aabom, A. et al. (2017) Complement factor C4 activation in patients with hereditary angioedema. Clinical Biochemistry 50 (15), 816-821.
3. Bork, K. and Davis-Lorton, M. (2013) Overview of hereditary angioedema caused by C1-inhibitor deficiency: assessment and clinical management. Eur Ann Allergy Clin Immunol 45 (1), 7-16.

4. Csuka, D. et al. (2017) The role of the complement system in hereditary angioedema. *Mol Immunol* 89, 59-68.
5. Li, H. H. et al. (2015) Comparison of chromogenic and ELISA functional C1 inhibitor tests in diagnosing hereditary angioedema. *J Allergy Clin Immunol Pract* 3 (2), 200-5.
6. Campbell, R. L., Wagner, D. B., and O'Connel, J. P. (1987). Solid phase assay with visual readout. U.S. Pat. No. 4,703,017.
7. Rosenstein, R. W. and Bloomster, T. G. (1989). Solid phase assay employing capillary flow. U.S. Pat. No. 4,855,240.
8. May, K., Prior, M. E., and Richards, I. (1997). Capillary immunoassay and device therefore comprising mobilizable particulate labelled reagents. U.S. Pat. No. 5,622,871.
9. O'Farrell, B. (2009). Evolution in Lateral Flow-Based Immunoassay Systems. In: Wong, R. C. and Tse, H. Y. (eds.). *Lateral Flow Immunoassay*. Humana Press New York (NY).
10. Zahedi R, Aulak K S, Eldering E, Davis A E 3rd (1996). Characterization of C1 inhibitor-Ta. A dysfunctional CHINH with deletion of lysine 251. *J Biol Chem.* 1996 Sep. 27; 271 (39): 24307-12

Example 3: Competitive Binding Assays Demonstrate Specificity of the Lateral Flow Assay (LFA) Device for Detecting Functional C1-Esterase Inhibitor (fC1-INH)

The specificity of the lateral flow assay (LFA) device as described herein for determining fC1-INH concentrations was examined by performing assays in the presence of different competitive binding proteins. Samples contained 100 mU/mL of purified C1-INH. No competing protein was added to the control sample. The intensity of the test line area was measured, and the percent reduction in signal from that of the control reaction was calculated for each sample. For samples with competing proteins, test line (TL) intensities were reduced between 40% to 60% compared to the control sample (Table 10). TL intensity was reduced 55% by the addition of biotin labeled BSA demonstrating that unrelated proteins are not detected in the assay (Table 10). TL intensities were reduced 61% and 48% for unlabeled FXIIa and unlabeled antibody, respectively, demonstrating specificity of FXIIa and antibody with C1-INH for signal production (Table 10).

TABLE 10

Results of specificity testing

| Test Line | Labeled Conjugate | Biotinylated Binding Protein | Competing Protein | Signal from 100 mU/mL | % Reduction in TL Signal |
|---|---|---|---|---|---|
| AbD28387 | Neutravidin-Eu | 50 nM FXIIa | None | 2400 | N/A |
|  |  |  | 3 µM BSA-biotin | 1080 | 55% |
|  |  |  | 200 nM FXIIa (no biotin) | 930 | 61% |
|  |  |  | 900 nM AbD28387 | 1240 | 48% |
| AbD28384 | Neutravidin-Eu | 50 nM FXIIa | None | 3700 | N/A |
|  |  |  | 900 nM AbD28384 | 2150 | 42% |

Specificity of detection was further tested using C1-INH protein that had been denatured by heating. TL intensity was not reduced by heating at 40° C., but heating at 53° C. reduced TL intensity to that of the background signal (Table 11).

TABLE 11

Results of specificity testing with heat treated C1-INH

| Test Line | Labeled Conjugate | Biotinylated Binding Protein | Heat Treatment | Signal from 1000 mU/mL in Plasma | Signal from Depleted Plasma |
|---|---|---|---|---|---|
| AbD28387 | Neutravidin-Eu | 50 nM FXIIa | None | 5410 | 360 |
|  |  |  | 40° C. for 120 min | 7110 | 360 |
|  |  |  | 53° C. for 120 min | 370 | 420 |

Taken together, these results demonstrate that the LFA and test strips described herein are specific for detection of fC1-INH in plasma samples.

Figure 10A:
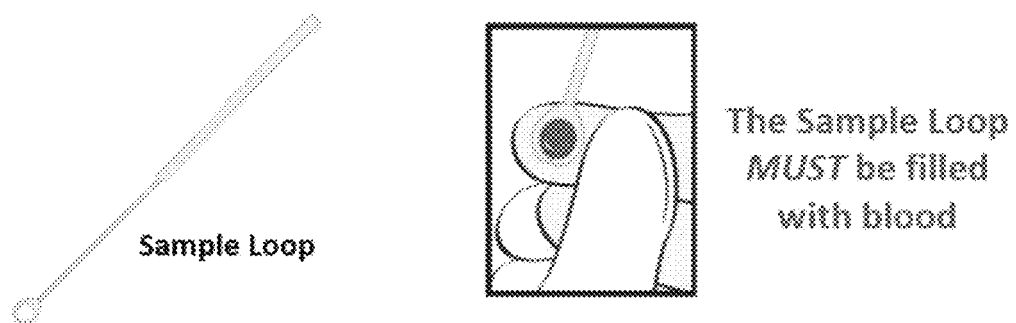
FIG. 10A is a schematic showing collection of a blood sample using a sample loop and fingerstick.
Figure 10B:
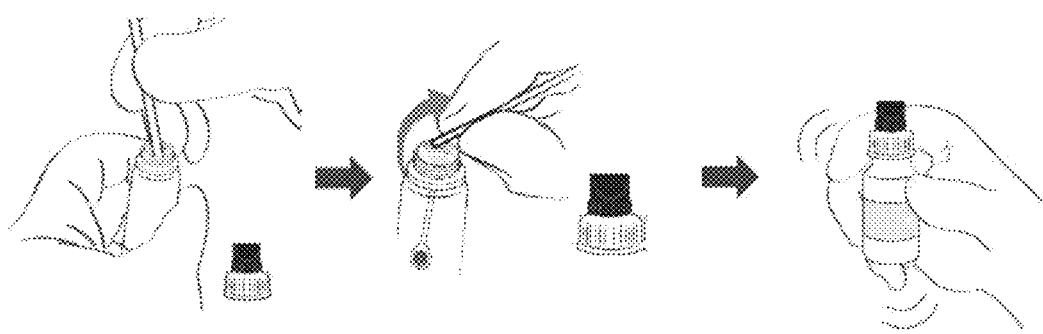
FIG. 10B is a schematic showing addition of a sample loop filled with blood of FIG. 10A to a SampleTainer® Bottle.

Example 4: Use of Blood Samples from Patients to Detect Functional C1-Esterase Inhibitor (fC1-INH) in LFA Device Briefly, a whole blood sample is collected by performing a fingerstick according to laboratory practices that would be evident to one of ordinary skill in the art. After wiping away the first blood droplet, a second blood droplet forms on the finger. A sample loop is used to contact the second blood droplet fill the loop with blood (FIG. 10A). The loop is then added to container, such as a SampleTainer® bottle (FIG. 10B). With the loop touching the bottom of the bottle, the bottle is snapped and twisted to break the bottom of the shaft into the bottle. Finally, the cap of the bottle is replaced and the bottle is shaken to mix. The whole blood sample may be added to any of the devices for analysis.

Example 5: Selection of Reagents

Figure 11A:
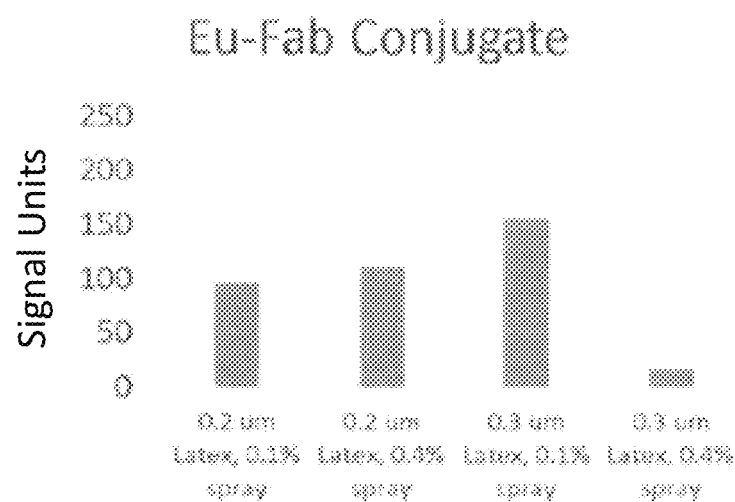
FIG. 11A is a graph showing use of an anti-C1-INH Fab conjugated to europium nanoparticles under the indicated conditions.
Figure 11B:
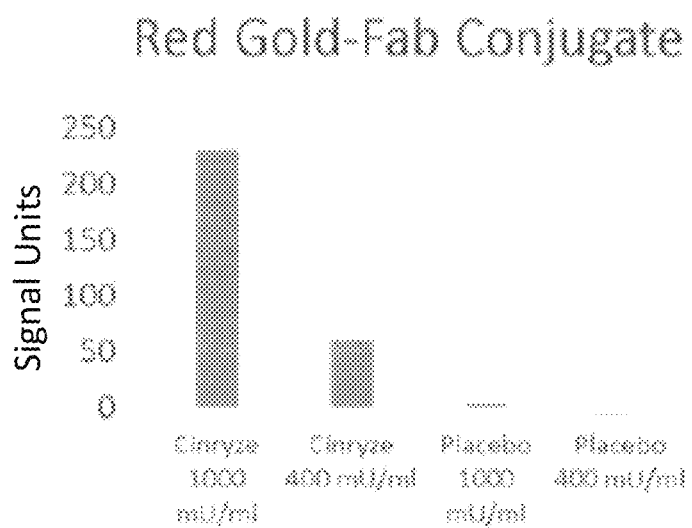
FIG. 11B is a graph showing use of an anti-C1-INH Fab conjugated to red gold nanoparticles under the indicated conditions.

Reagents were selected for use in the methods and/or with the devices described herein. Two initial detection agents were developed: one employing a europium nanoparticle conjugated to an anti-fC1-INH Fab (FIG. 11A) and one using a Red Gold nanoparticle conjugated to an anti-fC1-INH Fab (FIG. 11B).

Figure 12:
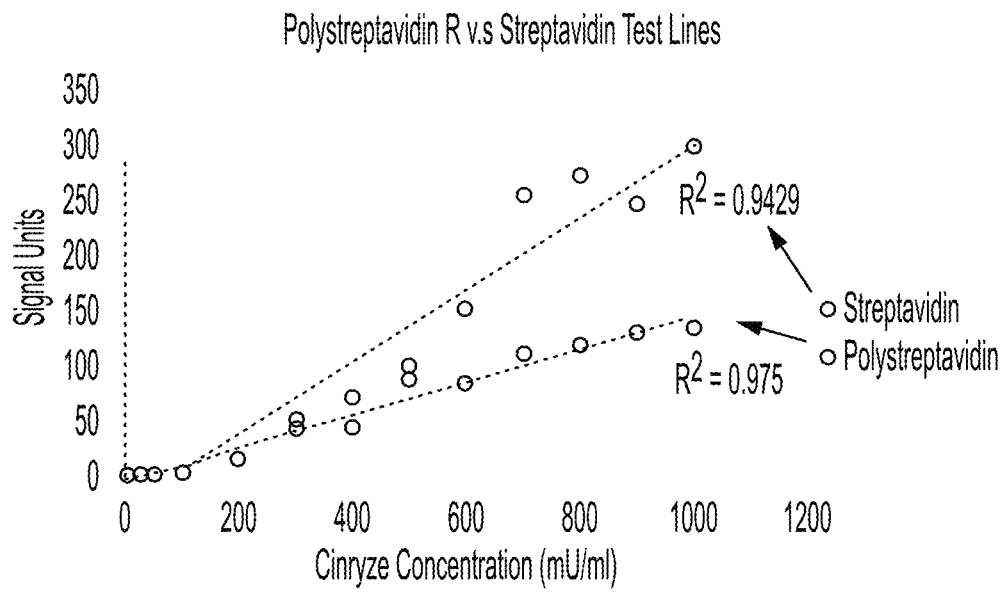
FIG. 12 is a graph showing results from polystreptavidin R compared to streptavidin as capture agents in the test line. $R^2$ value indicates the fit to the model line (dotted line).

A steep decrease in signal at the lower end of the dynamic range was observed, suggesting that the system was reaching the maximum signal. In effort to decrease the slope of the relationship, different amounts of different reagents were evaluated. Two reagents were assessed as Test Lines: streptavidin and polymeric version of streptavidin (polystreptavidin R) printed at a concentration of 0.5 mg/mL. Stretptavidin was found to have higher signals as compared to polystreptavidin, whereas polystreptavidin was found to have more linearity (FIG. 12). Europium conjugates were adjusted to 0.05% solids from 0.1%. The concentration of FXIIa used in the incubation step with C1-INH/CINRYZE® was reduced from 1 pmol/µL to 0.5 pmol/µL to reduce the dynamic range of the assay. This resulted in an assay with a signal within a detectable range.

Figure 13:
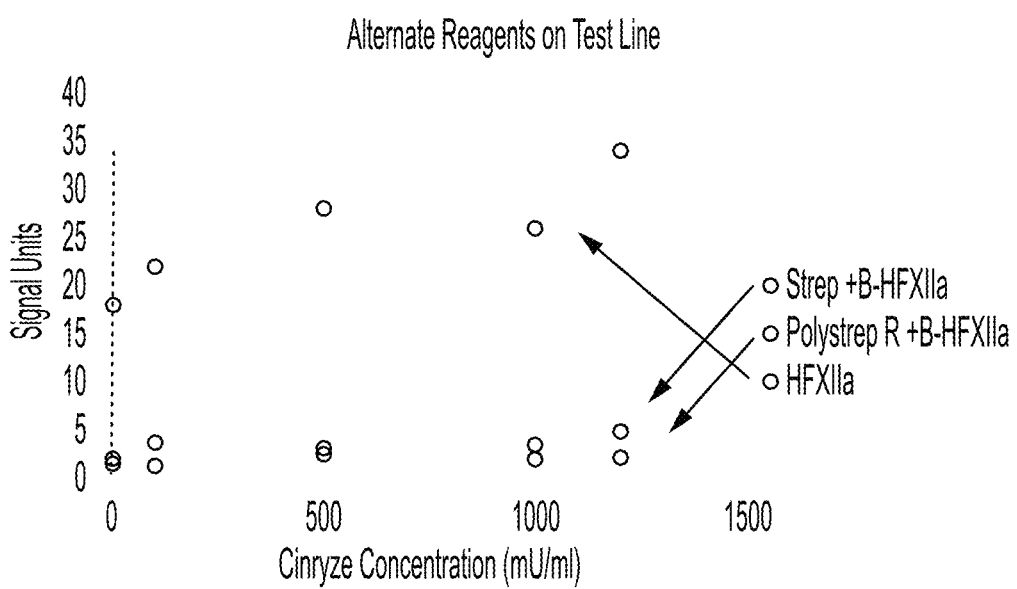
FIG. 13 is a graph showing results from use of the indicated reagents as capture agents in the test line.

Different agents were also assessed for the test lines. Briefly, three different test lines were generated: human biotinylated FXIIa (B-HFXIIa) was mixed with streptavidin, B-HFXIIa was mixed with polystreptavidin, and HFXIIa (non-biotinylated) alone. Use of HFXIIa provided a positive, yet low, signal whereas B-HFXIIa and streptavidin and B-HPFXIIa and polystreptavidin did not have any appreciable positive signal (FIG. 13).

Figure 14:
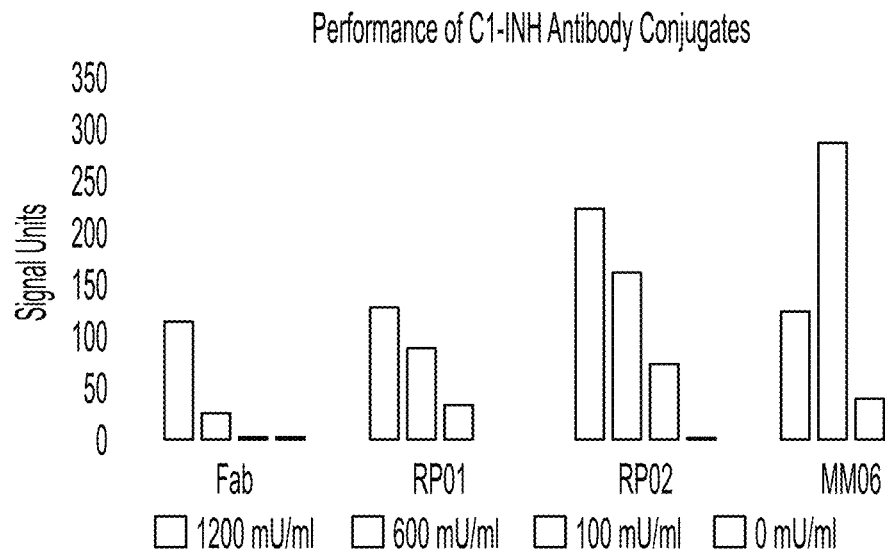
FIG. 14 is a graph showing results from the indicated anti-C1-INH Fab or antibody clones as detection agents. For each antibody, columns refer to concentrations of the detection agent, from left to right, 1200 mU/mL, 600 mU/mL, 100 mU/mL, 0 mU/mL.

Additionally, anti-C1-INH antibodies were also evaluated for use in the methods described herein. Four europium conjugates (the anti-C1-INH Fab as well as anti-C1-INH antibodies RP01, RP02, MM03 and MM06 antibodies from Sino Biological Inc.) were evaluated at four concentrations (1200 mU/mL, 600 mU/mL, 100 mU/mL, and 9 mU/mL) (FIG. 14). The signal obtained using each of antibodies RP01, RP02, MM03 and MM06 was enhanced as compared to the Fab conjugate. Polyclonal antibody RP02 was selected for further analysis.

Figure 15:
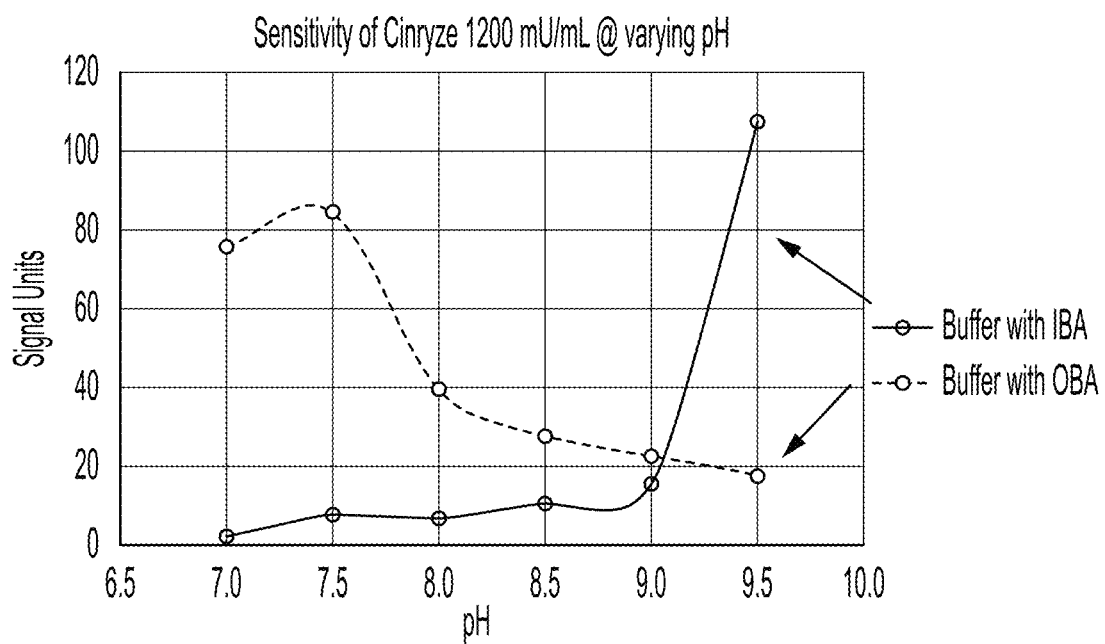
FIG. 15 is a graph showing results using a buffer containing inorganic blocking agent (IBA) or organic blocking agent (OBA) at various pH.

Buffer conditions were also evaluated. For example, a buffer with inorganic buffer agent (IBA) or a buffer with organic buffer agent (OBA) were each prepared at different pH from 7.0-9.5. The buffer with the IBA performed better (e.g., higher signal) at the higher end of the pH range (pH 9.5), whereas the buffer with the OBA performed better (e.g., higher signal) at physiological pH ranges (around 7-7.5) (FIG. 15).

Figure 16:
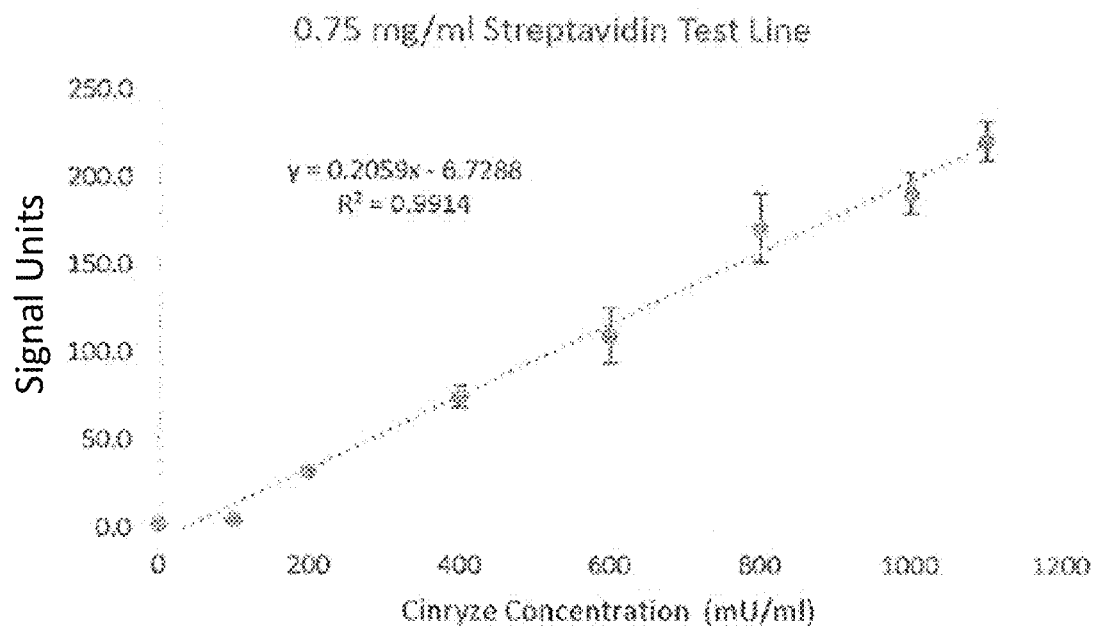
FIG. 16 is a graph showing results using a streptavidin test line (0.75 mg/mL streptavidin) and the indicated concentrations of C1-INH/CINRYZE®.

Finally, the detectable agent conjugated to the anti-C1-INH binding agent was also evaluated. In particular, antibody RP02 was assessed using an europium conjugate or a red gold conjugate and compared to the anti-C1-INH Fab. The Fab conjugates did not result in positive signals, whereas the RP02 antibodies with red gold conjugates resulted in positive signal (FIG. 16).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present disclosure, and without departing from the spirit and scope thereof, can make various changes and modifications of the present disclosure to adapt it to various usages and conditions. Thus, other embodiments are also within the claims.

EQUIVALENTS AND SCOPE

Those skilled in the art will recognize, or be able to ascertain using no more than routine experimentation, many equivalents to the specific embodiments of the present disclosure described herein. The scope of the present disclosure is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The present disclosure includes embodiments in which exactly one member of the group is present in, employed in, or otherwise relevant to a given product or process. The present disclosure includes embodiments in which more than one, or all of the group members are present in, employed in, or otherwise relevant to a given product or process.

Furthermore, the present disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the present disclosure, or aspects of the present disclosure, is/are referred to as comprising particular elements and/or features, certain embodiments of the present disclosure or aspects of the present disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the present disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the present disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A device for detecting and/or quantifying functional C1-esterase inhibitor (fC1-INH) in a human sample, the device comprising:
   (i) a conjugate pad comprising a first zone and a second zone, wherein the first zone comprises a first agent and the second zone comprises a second agent, and
   (ii) a membrane, which is in communication with the conjugate pad, wherein the membrane comprises a third zone, on which a third agent is immobilized,
   wherein the first agent is a functional C1 inhibitor (fC1-INH) binding agent or a C1 inhibitor (C1-INH) binding agent and the second agent is a fC1-INH binding agent or a C1-INH binding agent,
   the first agent and the second agent being different from each other;
   wherein the third agent is a capture agent capable of binding to a docking agent,
   wherein one of the fC1-INH binding agent and the C1-INH binding agent is conjugated to a detectable label, and one of the fC1-INH binding agent and the C1-INH binding agent is conjugated to the docking agent, the detectable label and the docking agent being conjugated to a different agent; and
   wherein the conjugate pad further comprises a fourth zone for placing the human sample, which flows through the device in the order of the first zone, the second zone, and the third zone.

2. The device of claim 1, wherein:
   (i) the first agent, the second agent, and the third agent are the C1-INH binding agent, the fC1-INH binding agent, and the capture agent, respectively, or wherein the first agent, the second agent, and the third agent are the fC1-INH binding agent, the C1-INH binding agent, and the capture agent, respectively;
   (ii) the first agent is conjugated to a detectable label, the second agent is conjugated to a docking agent, or wherein the first agent is conjugated to a docking agent, the second agent is conjugated to a detectable label;
   (iii) the docking agent and the capture agent are members of a receptor-ligand pair.

3. The device of claim 2, wherein
   the receptor-ligand pair comprises biotin and avidin.

4. The device of claim 3, wherein the docking agent is biotin and the capture agent is avidin.

5. The device of claim 4, wherein the avidin is streptavidin or polystreptavidin.

6. The device of claim 1, wherein the detectable label is selected from the group consisting of europium, colloidal gold, phycoerythrin, fluorescein, rhodamine, green fluorescent protein, quantum dot, and chromophore.

7. The device of claim 1, wherein
   the first agent is the C1-INH binding agent located at the first zone, the second agent is the fC1-INH binding agent located at the second zone, and the third agent is the capture agent located at the third zone.

8. The device of claim 7, wherein
   the C1-INH binding agent is an antibody binding to C1-INH, which is conjugated to the detectable label, the fC1-INH binding agent is FXIIa conjugated to the docking agent, which is biotin, and the capture agent is an avidin, which optionally is streptavidin or polystreptavidin.

9. The device of claim 1, further comprising:
   (i) an absorbent pad in communication with the membrane, wherein the absorbent pad and the conjugate pad are separated by the membrane;
   (ii) a support member, on which the conjugate pad, the membrane, and/or the absorbent pad is mounted; and/or
   (iii) a housing.

10. The device of claim 9, wherein the housing comprises a first opening to form a buffer port, a second opening to form a sample port, and a third opening to form a test window.

11. The device of claim 10, wherein:
    (i) the sample port is located between the buffer port and the test window;
    (ii) the buffer port aligns with the first zone, on which the C1-INH binding agent is located;
    (iii) the sample port aligns with the second zone, on which the fC1-INH binding agent is located; and/or
    (iv) the test window aligns with the third zone, on which the capture agent is located.

12. A method for detecting and/or quantifying functional C1-esterase inhibitor (fC1-INH) in a human sample, the method comprising:
    (i) placing the human sample in the sample port of the device of claim 10,
    (ii) placing a buffer in the buffer port in the device, wherein the buffer flows in the direction from the first zone to the third zone;
    (iii) examining a signal at the test window in the device, and
    (iv) determining presence or measuring the level of fC1-INH in the human sample based on presence or intensity of the signal at the test window.

13. The method of claim 12, wherein step (ii) is performed at least at least 5 minutes after step (i), and wherein the second zone comprises the fC1-INH binding agent and aligns with the sample port.

14. The method of claim 12, wherein:
 (a) the human sample is obtained from a human subject; and/or
 (b) the human subject is suspected of having or at risk for a fC1-INH deficiency-mediated disorder.

15. The method of claim 14, wherein the human sample is a serum sample, a plasma sample, or a blood sample.

16. The method of claim 14, wherein
 the fC1-INH deficiency-mediated disorder is selected from the group consisting of hereditary angioedema (HAE), acquired angioedema (AAE), and a C1-INH related immune disease.

17. The method of claim 16, wherein:
 (a) the human subject has a symptom of HAE; and
 (b) the HAE is type I HAE or type II HAE; or
 (c) the human subject has no symptom of HAE, has no history of a symptom of HAE, or no history of HAE.

18. The device of claim 1, wherein the fC1-INH binding agent is an active form of Factor XII (FXIIa) and/or the C1-INH binding agent is an antibody that binds C1-INH.

19. The device of claim 1, wherein the fourth zone overlaps with the second zone.

20. The device of claim 1, wherein the detectable label is attached to latex particles.

* * * * *